(12) United States Patent
Rohling et al.

(10) Patent No.: US 12,714,404 B2
(45) Date of Patent: Aug. 25, 2026

(54) FLEXIBLE CAPACITIVE MICROMACHINED ULTRASONIC TRANSDUCER ARRAYS

(71) Applicant: THE UNIVERSITY OF BRITISH COLUMBIA, Vancouver (CA)

(72) Inventors: Robert Rohling, Vancouver (CA); Carlos D. Gerardo, Vancouver (CA); Edmond Cretu, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 818 days.

(21) Appl. No.: 17/758,932

(22) PCT Filed: Jan. 18, 2021

(86) PCT No.: PCT/CA2021/050052

§ 371 (c)(1), (2) Date: Jul. 15, 2022

(87) PCT Pub. No.: WO2021/142554

PCT Pub. Date: Jul. 22, 2021

(65) Prior Publication Data

US 2023/0042741 A1 Feb. 9, 2023

Related U.S. Application Data

(60) Provisional application No. 62/962,284, filed on Jan. 17, 2020, provisional application No. 62/962,285, (Continued)

(51) Int. Cl.
*A61B 8/00* (2006.01)
*A61B 6/50* (2024.01)
(Continued)

(52) U.S. Cl.
CPC ............ *A61B 8/5261* (2013.01); *A61B 6/502* (2013.01); *A61B 8/4416* (2013.01); (Continued)

(58) Field of Classification Search
None
See application file for complete search history.

(56) References Cited

U.S. PATENT DOCUMENTS 5,828,394 A 10/1998 Khuri-Yakub et al.
6,493,288 B2 12/2002 Khuri-Yakub et al.
(Continued)

FOREIGN PATENT DOCUMENTS

JP H05215694 A 8/1993
JP 2005021380 A 1/2005
(Continued)

OTHER PUBLICATIONS

Memon, Farah, et al. "Capsule ultrasound device: Further developments." 2016 IEEE International Ultrasonics Symposium (IUS). IEEE, 2016. (Year: 2016).*
(Continued)

*Primary Examiner* — Jonathan D Armstrong
(74) *Attorney, Agent, or Firm* — D'Ambrosio & Menon, PLLC; Usha Menon

(57) ABSTRACT

An apparatus comprising an array of polymer-based capacitive micromachined ultrasonic transducers positioned on a substrate. The substrate may be at least substantially transparent to ionizing radiation, be flexible, and/or have walls positioned thereon to protect the transducers.

26 Claims, 32 Drawing Sheets

Related U.S. Application Data filed on Jan. 17, 2020, provisional application No. 62/962,291, filed on Jan. 17, 2020.

(51) Int. Cl.
*B06B 1/02* (2006.01)
*B81B 3/00* (2006.01)
*G01N 29/24* (2006.01)

(52) U.S. Cl.
CPC .......... *B06B 1/0292* (2013.01); *B81B 3/0021* (2013.01); *G01N 29/2406* (2013.01); *B81B 2203/0127* (2013.01); *B81B 2203/0315* (2013.01); *B81B 2203/04* (2013.01); *B81B 2207/053* (2013.01)

(56) References Cited

U.S. PATENT DOCUMENTS 6,606,389 B1 8/2003 Selfridge et al.
6,854,338 B2 2/2005 Khuri-Yakub et al.
7,376,236 B1 5/2008 Norris et al.
7,615,834 B2 11/2009 Khuri-Yakub et al.
7,646,097 B2 1/2010 Yu et al.
7,673,375 B2 3/2010 Chang et al.
7,741,686 B2 6/2010 Khuri-Yakub et al.
7,745,973 B2 6/2010 Bayram et al.
7,759,839 B2 7/2010 Huang
8,451,693 B2 5/2013 Nikoozadeh et al.
9,132,693 B2 9/2015 Klootwijk et al.
9,586,233 B2 3/2017 Apte et al.
9,662,679 B2 5/2017 Chen et al.
10,123,782 B2 11/2018 Bhuyan et al.
10,509,013 B2 12/2019 Gerardo et al.
10,564,132 B2 2/2020 Gerardo et al.
10,598,632 B1 3/2020 Gerardo et al.
2003/0005771 A1 1/2003 Percin et al.
2003/0024317 A1 2/2003 Miller
2005/0101867 A1 5/2005 Johnson et al.
2005/0121734 A1* 6/2005 Degertekin ........... B06B 1/0292 438/48
2005/0146247 A1 7/2005 Fisher et al.
2005/0177045 A1* 8/2005 Degertekin ........ G01N 29/2406 600/447
2005/0219953 A1 10/2005 Bayram et al.
2007/0093702 A1 4/2007 Yu et al.
2007/0140515 A1* 6/2007 Oliver .................... H04R 23/00 381/174
2007/0287912 A1 12/2007 Khuri-Yakub et al.
2007/0295064 A1* 12/2007 Degertekin ............ G01Q 20/04 73/105
2008/0194053 A1 8/2008 Huang
2010/0107745 A1* 5/2010 Bonin ...................... G01N 3/42 73/105
2010/0168583 A1* 7/2010 Dausch ................. B06B 1/0622 600/466
2010/0173437 A1 7/2010 Wygant et al.
2010/0280388 A1 11/2010 Huang
2012/0133001 A1* 5/2012 Tkaczyk .............. A61B 8/4483 438/66
2012/0245457 A1* 9/2012 Crowley .............. A61B 8/4477 600/424
2013/0242705 A1 9/2013 Kim et al.
2013/0258803 A1* 10/2013 Nakamura ............. G03B 42/06 367/87
2014/0013850 A1 1/2014 Kim et al.
2014/0169527 A1 6/2014 Luo
2015/0182187 A1* 7/2015 Samset ................ A61B 8/4416 600/424
2016/0051225 A1 2/2016 Kim et al.
2017/0050217 A1 2/2017 Johnson et al.
2017/0090024 A1* 3/2017 Kitchens, II ......... A61B 8/0858
2018/0036558 A1 2/2018 Carpentier et al.
2018/0167740 A1* 6/2018 Uchida .................... H04R 9/08
2018/0276440 A1* 9/2018 Strohmann ........ G06V 40/1359
2018/0344167 A1 12/2018 Xiang
2019/0187101 A1 6/2019 Gerardo et al.
2020/0282424 A1 9/2020 Oralkan et al.
2021/0260622 A1* 8/2021 Lin ..................... B81C 1/00357

FOREIGN PATENT DOCUMENTS

JP 2008173291 A 7/2008
JP 2017018510 A 1/2017
JP 2017130952 A 7/2017
JP 2017201782 A 11/2017
KR 20190139027 A * 12/2019 ......... H01L 41/1876
WO 2019119127 A1 6/2019
WO 2021142554 7/2021
WO 2022067447 7/2022
WO WO-2024011328 A1 * 1/2024

OTHER PUBLICATIONS

Lucarini, Ivano, Luca Maiolo, and Alessandro S. Savoia. "Fabrication and characterization of capacitive micromachined ultrasonic transducers integrated on ultra-thin and flexible substrates." 2019 IEEE International Ultrasonics Symposium (IUS). IEEE, 2019. (Year: 2019).*

Anzinger, Sebastian. Airborne capacitive micromachined ultrasonic transducers in dual-backplate technology. Verlag Dr. Hut, 2022. (Year: 2022).*

Omidvar, Amirhossein. Flexible polymer-based capacitive micromachined ultrasonic transducers (polyCMUTs) for conformal sonography. Diss. University of British Columbia, 2024. (Year: 2024).*

Wang M et al.: "A photoacoustic imager with infrared illumination through the CMUT chip", 2011 16th International Solid-State Sensors, Actuators and Microsystems Conference (Transducers 2011); Beijing, China; Jun. 5-9, 2011, IEEE, Piscataway, JN, Jun. 5, 2011, pp. 2188-2191, XP031910730.

Oralkan, O. et al. Capacitive micromachined ultrasonic transducers: Next-generation arrays for acoustic imaging? Ultrasonics, Ferroelectrics and Frequency Control, IEEE Transactions on 49, 1596-1610 (2002).

S. Ergun, Y. Huang, X. Zhuang, O. Oralkan, G. G. Yarahoglu, and B. T. Khuri-Yakub, "Capacitive micromachined ultrasonic transducers: fabrication technology," Ultrasonics, Ferroelectrics and Frequency Control, IEEE Transactions on, vol. 52, No. 12, pp. 2242-2258, 2005.

A. Bozkurt, I. Ladabaum, A. Atalar, and B. T. Khuri-Yakub, "Theory and analysis of electrode size optimization for capacitive microfabricated ultrasonic transducers," IEEE Transactions on Ultrasonics, Ferroelectrics, and Frequency Control, vol. 46, No. 6, pp. 1364-1374, Nov. 1999.

M. M. Chang, M. T. Deng, J. T. Gwo, J. D. Mai and E. Hsu, "Polymer-based Capacitive Micromachined Ultrasonic Transducers (CMUT) for Micro Surgical Imaging Applications," 2006 1st IEEE International Conference on Nano/Micro Engineered and Molecular Systems, Zhuhai, pp. 61-65, 2006.

D.A. Hutchins, D.R. Billson, R.J. Bradley, K.S. Ho. Structural health monitoring using polymer-based capacitive micromachined ultrasonic transducers (CMUTs). Ultrasonics, vol. 51, No. 8, pp. 870-877, 2011.

H. Lorenz, M. Despont, N. Fahrni, N. LaBianca, P. Renaud, and P. Vettiger, "SU-8: a low-cost negative resist for MEMS," J. Micromech. Microeng., vol. 7, No. 3, p. 121, 1997.

C. Liu, "Recent Developments in Polymer MEMS," Adv. Mater., vol. 19, No. 22, pp. 3783-3790, Nov. 2007.

Y. P. Li, C. D. He, J. T. Zhang, J. L. Song, W. D. Zhang, and C. Y. Xue, "Design and Analysis of Capacitive Micromachined Ultrasonic Transducers Based on SU-8," Key Engineering Materials, vol. 645-646, pp. 577-582, May 2015.

Joseph, J., Singh, S. G. & Vanjari, S. R. K. Fabrication of SU-8 based Capacitive Micromachined Ultrasonic Transducer for low frequency therapeutic applications. in 2015 37th Annual Interna-

(56) References Cited

OTHER PUBLICATIONS tional Conference of the IEEE Engineering in Medicine and Biology Society (EMBC) 1365-1368 (2015). doi:10.1109/EMBC.2015.7318622.

Chiou, D.-Y., Chen, M.-Y., Chang, M.-W. & Deng, H.-C. Finite element modeling, characterization, and optimization design for the polymer-typed capacitive micro-arrayed ultrasonic transducer. Microsyst Technol 14, 787-797 (2008).

C. F. Dalziel, “Electric shock hazard,” IEEE Spectrum, vol. 9, No. 2, pp. 41-50, Feb. 1972.

Li, Z., Ilkhechi, A. K., Ceroici, C. & Zemp, R. Transparent capacitive micromachined ultrasonic transducer (CMUT) arrays for real-time photoacoustic applications. Opt. Express, OE 27, 13204-13218 (2019).

A. Gefen and B. Dilmoney, “Mechanics of the normal woman’s breast,” THC, vol. 15, No. 4, pp. 259-271, Jul. 2007.

* cited by examiner

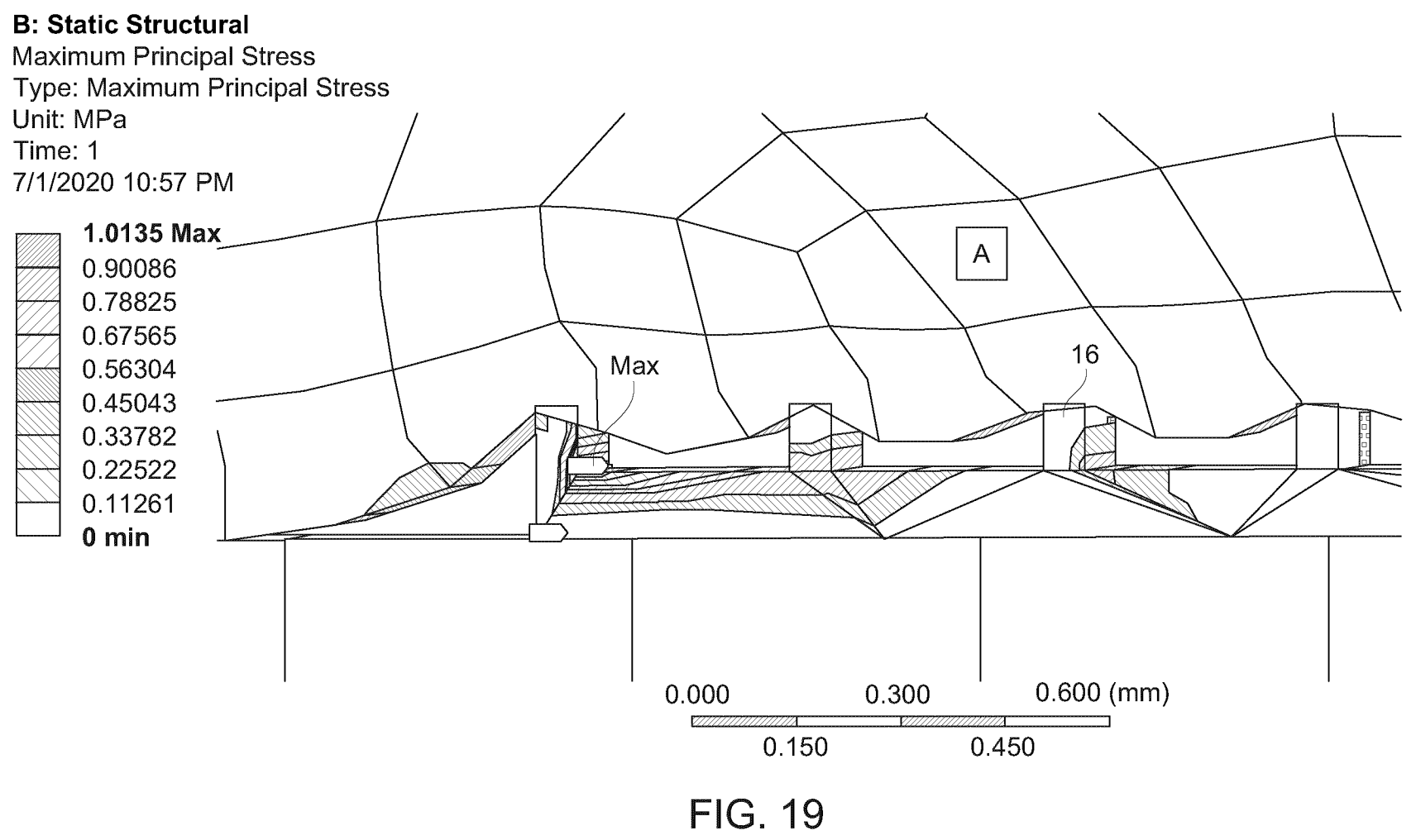

B: Static Structural
Maximum Principal Stress
Type: Maximum Principal Stress
Unit: MPa
Time: 1
7/1/2020 10:57 PM

1.0135 Max
0.90086
0.78825
0.67565
0.56304
0.45043
0.33782
0.22522
0.11261
0 min

A
16
Max 0.000 0.150 0.300 0.450 0.600 (mm)

FIG. 19

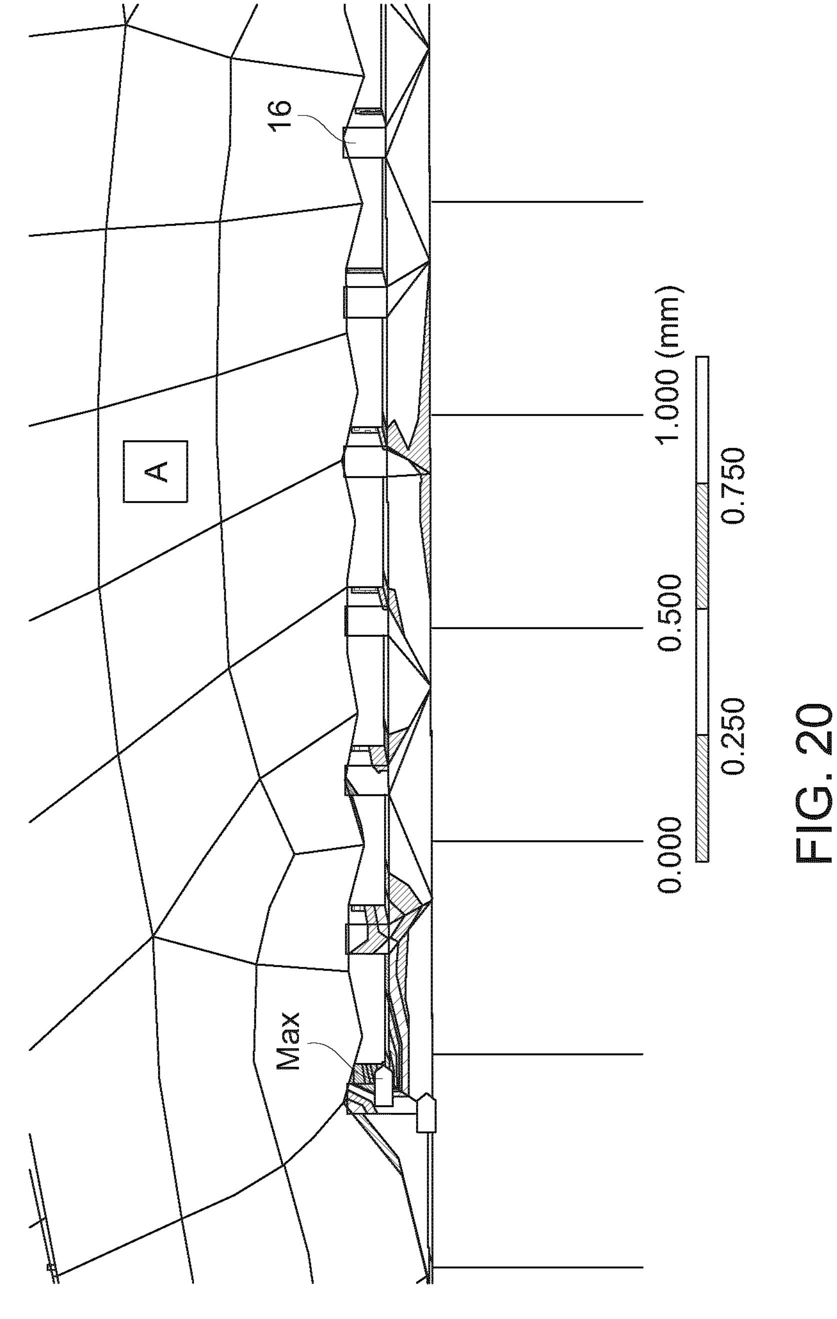
FIG. 20
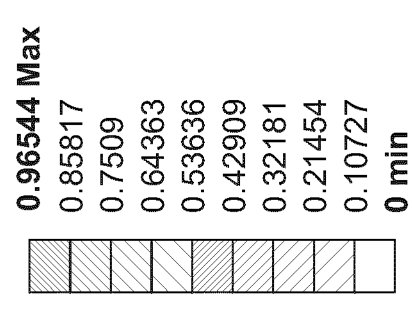

Figure 21:
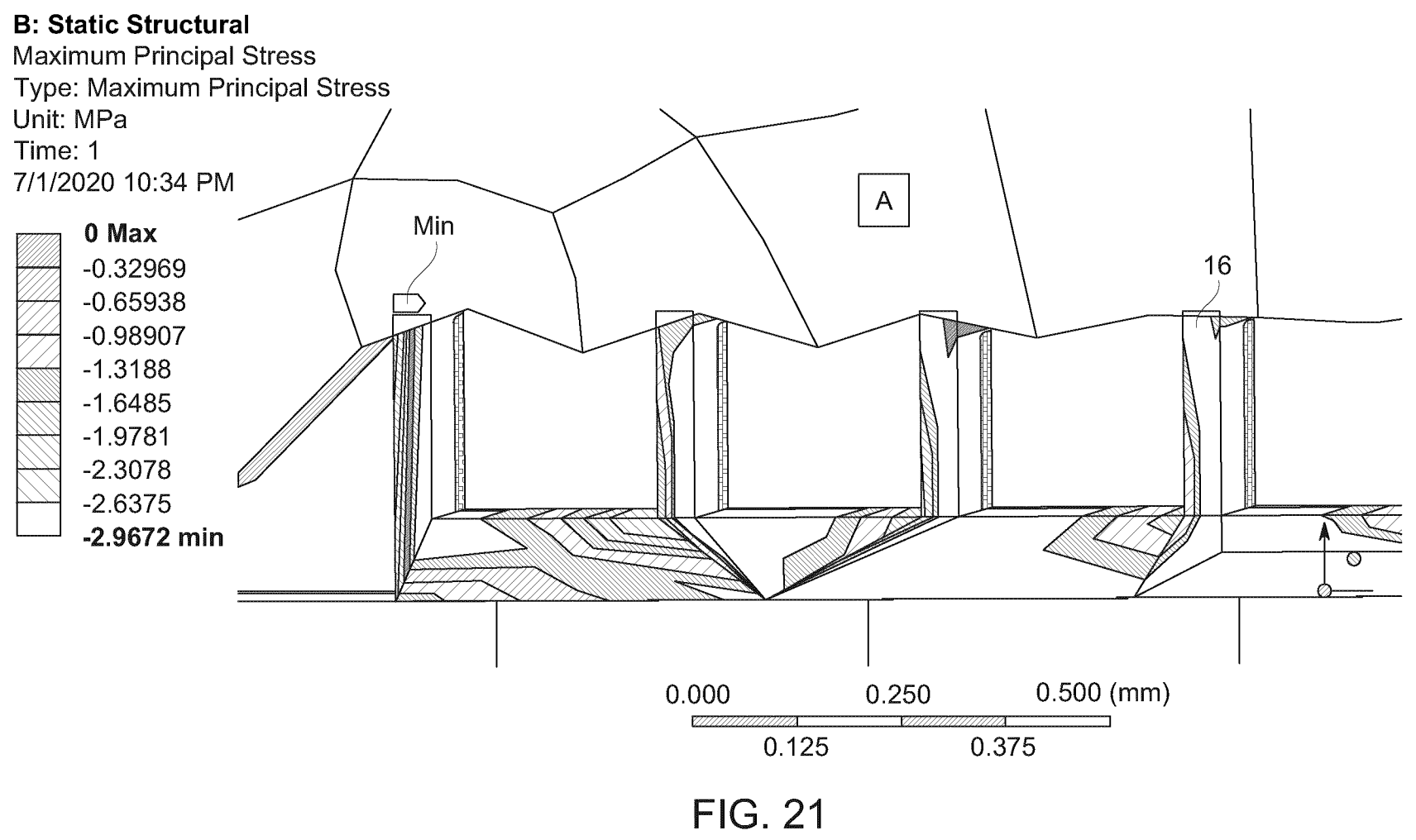

B: Static Structural
Maximum Principal Stress
Type: Maximum Principal Stress
Unit: MPa
Time: 1
7/1/2020 10:34 PM

0 Max
-0.32969
-0.65938
-0.98907
-1.3188
-1.6485
-1.9781
-2.3078
-2.6375
-2.9672 min

Min
A
16

Sample under mammography system

FLEXIBLE CAPACITIVE MICROMACHINED ULTRASONIC TRANSDUCER ARRAYS

CROSS-REFERENCE TO RELATED APPLICATIONS

This application claims priority under 35 U.S.C. § 119 (e) to U.S. provisional patent application No. 62/962,284 filed on Jan. 17, 2020, and entitled "Wearable CMUT monitor"; U.S. provisional patent application No. 62/962,285 filed on Jan. 17, 2020, and entitled "Flexible Capacitive Micromachined Ultrasonic Transducer Fabric"; and U.S. provisional patent application No. 62/962,291 filed on Jan. 17, 2020, and entitled "Transparent Polymer-based Capacitive Micromachined Ultrasonic Transducers", the entireties of all of which are hereby incorporated by reference in those jurisdictions allowing such incorporation.

BACKGROUND

(a) Field

The subject matter disclosed generally relates to capacitive micromachined ultrasonic transducer arrays, specifically large flexible arrays for non-destructive testing (NDT) of three-dimensional inanimate structures including bridge supports, pipelines, and aircraft wings; flexible garments for human monitoring and therapy, and x-ray-transparent components for tissue diagnostics, particularly in association with x-ray machines.

(b) Related Prior Art

Ultrasound imaging is the most widely used medical imaging modality in the world in terms of images created annually. In ultrasound imaging, ultrasonic waves emitted by a transducer travel through a material and reflect off of interfaces to other materials with different acoustic impedances. The reflected echoes travel back to a transducer where they are processed to form an ultrasound image. Ultrasound transducers transform electrical voltage into acoustic waves and vice versa.

Ultrasound systems have traditionally used piezoelectric materials for their transducers since the 1930s. Materials such as piezoelectric crystals (e.g., quartz), ceramics (e.g., lead zirconate titanate (PZT)), and polymers (e.g., polyvinylidene fluoride (PVDF)) have been used as the transducer materials [1]. Despite the fact that piezoelectric transducers technology is mature, it suffers many drawbacks, such as the technical challenges in fabricating large two-dimensional arrays due to interconnection and integration challenges [1] at the die-level.

Acoustic impedance (speed of sound in a material multiplied by its density, measured in Rayls) is a measure of the opposition that a system presents to the acoustic pressure applied to the system. It is an important quantity in piezoelectric-based ultrasound systems, since it determines how much acoustic power is effectively transferred to a target material being imaged. An "acoustic matching layer" is a mandatory structure in piezoelectric-based systems to reduce the impedance mismatch between the impedance of the crystals and lower or higher impedance of the target materials (e.g., tissues or metals). These matching layers are typically made of high-density rubber combined with liquid gel, and are located between the crystals and the target material.

Capacitive Micromachined Ultrasound Transducers (CMUTs) are deemed to be an alternative technology to the current piezoelectric-based transducers [1]. A CMUT is essentially a parallel-plate capacitor with a fixed electrode at the bottom fixed to a substrate, with a suspended membrane over a cavity and sealed along the edges. A metallic electrode is patterned on top of the suspended membrane. Ultrasound waves are generated by a CMUT when an AC signal superimposed on a DC voltage is applied between both electrodes; alternately, ultrasound waves can be detected by measuring the variation in capacitance of the device while a DC voltage is applied in the presence of incoming ultrasound. Most CMUTs are made of silicon material on a silicon substrate. Silicon has a higher acoustic impedance than soft tissue, and a lower acoustic impedance than metals or composites, so there is still a mismatch.

The inventors have previously developed a polymer-based manufacturing technology (U.S. Pat. Nos. 10,509,013B2, 10,564,132B2 and 10,598,632B1 by Gerardo, Rohling and Cretu, the entireties of all of which are hereby incorporated by reference herein) that allows the microfabrication of ultrasonic transducers using polymer membranes, reducing as well the required operating voltages.

SUMMARY

According to one aspect, there is provided (i) a substrate; (ii) an array of polymer-based capacitive micromachined ultrasonic transducers positioned on the substrate, the array comprising a first row of the transducers and electrical interconnections electrically connecting the transducers of the first row in series; and (iii) two rows of walls extending from a same side of the substrate as the transducers and positioned such that the first row of the transducers is between the two rows of walls, wherein the walls are taller than the transducers.

The array may further comprise additional rows of the transducers and electrical interconnections electrically connecting the transducers of any one of the additional rows in series with each other, and the apparatus may further comprise additional rows of walls extending from a same side of the substrate as the additional rows of the transducers and positioned such that the additional rows of the transducers are respectively between the additional rows of walls, wherein the additional rows of walls are taller than the additional rows of the transducers.

The rows of transducers may be positioned in parallel with each other.

The apparatus may further comprise electrical interconnections spanning across the walls such that the transducers comprise an electrically interconnected matrix.

The apparatus may further comprise columns of walls extending from the same side of the substrate as the transducers and that cross the rows of walls, wherein columns of the transducers are respectively between the columns of walls, and wherein the columns of walls are taller than the transducers.

The walls may reduce acoustic cross-coupling.

At least some of the walls may be segmented.

The transducers may comprise dyed polymer.

The substrate may be flexible.

A portion of the side of the substrate on which the array of transducers is positioned may be adhesive, and the portion that is adhesive may be located around the array.

The substrate may comprise an elastic fabric.

The substrate may comprise a metal foil.

The substrate may be substantially transparent to ionizing radiation.

The ionizing radiation may be x-rays.

The substrate may have a transmissivity to x-rays of at least 77.4%

The apparatus may further comprise fiducial markers located on at least one corner of the substrate, wherein the fiducial markers are less transparent to x-rays than the substrate.

The substrate may be non-magnetic.

The substrate may be substantially transparent to at least one of ultraviolet light, visible light, and infrared light.

The substrate may comprise polyimide, polycarbonate, polymethyl methacrylate, aluminum, and/or Indium Tin Oxide.

The walls may have a height of at least 50 μm.

At least some of the walls may extend linearly across the substrate.

At least some of the walls may extend in a zig-zag pattern across the substrate.

At least some of the walls may be mechanically reinforced.

The walls that are mechanically reinforced may comprise reinforced portions and non-reinforced portions in which the reinforced portions are thicker than the non-reinforced portions, and wherein at least the ends of the walls comprise the reinforced portions.

The walls that are mechanically reinforced may comprise reinforced portions and non-reinforced portions in which the reinforced and non-reinforced portions have different cross-sections.

The walls that are mechanically reinforced may comprise reinforced portions and non-reinforced portions in which the reinforced and non-reinforced portions are manufactured from different materials.

The apparatus may further comprise acoustic micro lenses, the acoustic micro lenses comprising one or more layers of material deposited between a top of the walls and a top of the transducers.

The substrate may comprise a tape for applying in rows to an object, wherein the tape comprises top bondpads along a top surface of the tape, bottom bondpads along a bottom surface of the tape, and vias through the tape respectively electrically connecting pairs of the top and bottom bondpads, wherein the bondpads are positioned such that the adjacent rows of the tape overlap each other and the top bondpads of one of the adjacent rows contact the bottom bondpads of the other of the adjacent rows.

The top and bottom bondpads respectively extend along edges of the top and bottom surfaces.

The rows of the transducers may extend non-orthogonally relative to edges of the tape to facilitate the applying of the tape to a curved surface.

The tape may comprise a relief alignment lock-in pattern positioned to facilitate overlapping of the bondpads.

The relief alignment lock-in pattern may comprise a protrusion on one of the top and bottom surfaces and a corresponding recess in the other of the top and bottom surfaces.

The apparatus may further comprise light waveguides embedded in the substrate.

The light waveguides may terminate in the transducers.

The light waveguides may terminate in the substrate outside of the transducers.

The apparatus may further comprise: (i) a wireless transmitter communicatively coupled to the transducers; and (ii) a battery electrically coupled to the wireless transmitter and to the transducers, wherein the wireless transmitter is configured to wirelessly transmit ultrasound data obtained using the transducers to a controller.

According to another aspect, there is provided an apparatus comprising: (i) a flexible substrate; and (ii) an array of polymer-based capacitive micromachined ultrasonic transducers positioned on the substrate, the array comprising a first row of the transducers and electrical interconnections electrically connecting the transducers of the first row in series.

The array may further comprise additional rows of the transducers and electrical interconnections electrically connecting the transducers of any one of the additional rows in series with each other.

The rows may be positioned in parallel with each other.

The apparatus may further comprise electrical interconnections spanning across the rows such that the transducers comprise an electrically interconnected matrix.

The transducers may comprise dyed polymer.

A portion of the side of the substrate on which the array of transducers is positioned may be adhesive, and the portion that is adhesive may be located around the array.

The substrate may comprise an elastic fabric.

The substrate may comprise a metal foil.

The substrate may be substantially transparent to ionizing radiation.

The ionizing radiation may be x-rays.

The substrate may have a transmissivity to x-rays of at least 77.4%.

The apparatus may further comprise fiducial markers located on at least one corner of the substrate, wherein the fiducial markers are less transparent to x-rays than the substrate.

The substrate may be non-magnetic and/or substantially transparent to at least one of ultraviolet light, visible light, and infrared light.

The substrate may comprise polyimide, polycarbonate, polymethyl methacrylate, aluminum, and/or Indium Tin Oxide.

The apparatus may further comprise two rows of walls extending from a same side of the substrate as the transducers of the first row and positioned such that the first row of the transducers is between the two rows of walls, wherein the walls are taller than the first row of transducers.

The array may further comprise additional rows of the transducers and electrical interconnections electrically connecting the transducers of any one of the additional rows in series with each other. The apparatus may further comprise additional rows of walls extending from a same side of the substrate as the additional rows of the transducers and positioned such that the additional rows of the transducers are respectively between the additional rows of walls, wherein the additional rows of walls are taller than the additional rows of the transducers.

The apparatus may further comprise columns of walls extending from the same side of the substrate as the transducers and that cross the rows of walls. The columns of the transducers may be respectively between the columns of walls, and the columns of walls may be taller than the transducers.

The walls may reduce acoustic cross-coupling.

At least some of the walls may be segmented.

The walls may have a height of at least 50 μm.

At least some of the walls may extend linearly across the substrate.

At least some of the walls may extend in a zig-zag pattern across the substrate.

At least some of the walls may be mechanically reinforced.

The walls that are mechanically reinforced may comprise reinforced portions and non-reinforced portions in which the reinforced portions are thicker than the non-reinforced portions, and at least the ends of the walls may comprise the reinforced portions.

The walls that are mechanically reinforced may comprise reinforced portions and non-reinforced portions in which the reinforced and non-reinforced portions have different cross-sections.

The walls that are mechanically reinforced may comprise reinforced portions and non-reinforced portions in which the reinforced and non-reinforced portions are manufactured from different materials.

The apparatus may further comprise acoustic micro lenses, and the acoustic micro lenses may comprise one or more layers of material deposited between a top of the walls and a top of the transducers.

The substrate may comprise a tape for applying in rows to an object, wherein the tape comprises top bondpads along a top surface of the tape, bottom bondpads along a bottom surface of the tape, and vias through the tape respectively electrically connecting pairs of the top and bottom bondpads. The bondpads may be positioned such that the adjacent rows of the tape overlap each other and the top bondpads of one of the adjacent rows contact the bottom bondpads of the other of the adjacent rows.

The top and bottom bondpads may respectively extend along edges of the top and bottom surfaces.

The rows of the transducers may extend non-orthogonally relative to edges of the tape to facilitate the applying of the tape to a curved surface.

The tape may comprise a relief alignment lock-in pattern positioned to facilitate overlapping of the bondpads.

The relief alignment lock-in pattern may comprises a protrusion on one of the top and bottom surfaces and a corresponding recess in the other of the top and bottom surfaces.

The apparatus may further comprise light waveguides embedded in the substrate.

The light waveguides may terminate in the transducers.

The light waveguides may terminate in the substrate outside of the transducers.

The apparatus may further comprise: (i) a wireless transmitter communicatively coupled to the transducers; and (ii) a battery electrically coupled to the wireless transmitter and to the transducers, wherein the wireless transmitter is configured to wirelessly transmit ultrasound data obtained using the transducers to a controller.

According to another aspect, there is provided an apparatus comprising: (i) a substrate at least 77.4% transparent to ionizing radiation; and (ii) an array of polymer-based capacitive micromachined ultrasonic transducers positioned on the substrate, the array comprising a first row of the transducers and electrical interconnections electrically connecting the transducers of the first row in series.

The ionizing radiation may be x-rays.

The apparatus may further comprise fiducial markers located on at least one corner of the substrate, wherein the fiducial markers are less transparent to x-rays than the substrate.

The array may further comprise additional rows of the transducers and electrical interconnections electrically connecting the transducers of any one of the additional rows in series with each other.

The rows may be positioned in parallel with each other.

The apparatus may further comprise electrical interconnections spanning across the rows such that the transducers comprise an electrically interconnected matrix.

The transducers may comprise dyed polymer.

A portion of the side of the substrate on which the array of transducers is positioned may be adhesive, and the portion that is adhesive may be located around the array.

The substrate may be flexible, non-magnetic, and/or substantially transparent to at least one of ultraviolet light, visible light, and infrared light.

The substrate may comprise an elastic fabric, a metal foil, polyimide, polycarbonate, polymethyl methacrylate, aluminum, and/or Indium Tin Oxide.

The apparatus may further comprise two rows of walls extending from a same side of the substrate as the transducers of the first row and positioned such that the first row of the transducers is between the two rows of walls, wherein the walls are taller than the first row of transducers.

The array may further comprise additional rows of the transducers and electrical interconnections electrically connecting the transducers of any one of the additional rows in series with each other. The apparatus may further comprise additional rows of walls extending from a same side of the substrate as the additional rows of the transducers and positioned such that the additional rows of the transducers are respectively between the additional rows of walls, wherein the additional rows of walls are taller than the additional rows of the transducers.

The apparatus may further comprise columns of walls extending from the same side of the substrate as the transducers and that cross the rows of walls. The columns of the transducers may be respectively between the columns of walls, and the columns of walls may be taller than the transducers.

The walls may reduce acoustic cross-coupling.

At least some of the walls may be segmented.

The walls may have a height of at least 50 μm.

At least some of the walls may extend linearly across the substrate.

At least some of the walls may extend in a zig-zag pattern across the substrate.

At least some of the walls may be mechanically reinforced.

The walls that are mechanically reinforced may comprise reinforced portions and non-reinforced portions in which the reinforced portions are thicker than the non-reinforced portions, and at least the ends of the walls may comprise the reinforced portions.

The walls that are mechanically reinforced may comprise reinforced portions and non-reinforced portions in which the reinforced and non-reinforced portions have different cross-sections.

The walls that are mechanically reinforced may comprise reinforced portions and non-reinforced portions in which the reinforced and non-reinforced portions are manufactured from different materials.

The apparatus may further comprise acoustic micro lenses, and the acoustic micro lenses may comprise one or more layers of material deposited between a top of the walls and a top of the transducers.

The substrate may comprise a tape for applying in rows to an object, wherein the tape comprises top bondpads along a top surface of the tape, bottom bondpads along a bottom surface of the tape, and vias through the tape respectively electrically connecting pairs of the top and bottom bondpads. The bondpads may be positioned such that the adjacent rows of the tape overlap each other and the top bondpads of one of the adjacent rows contact the bottom bondpads of the other of the adjacent rows.

The top and bottom bondpads may respectively extend along edges of the top and bottom surfaces.

The rows of the transducers may extend non-orthogonally relative to edges of the tape to facilitate the applying of the tape to a curved surface.

The tape may comprise a relief alignment lock-in pattern positioned to facilitate overlapping of the bondpads.

The relief alignment lock-in pattern may comprise a protrusion on one of the top and bottom surfaces and a corresponding recess in the other of the top and bottom surfaces.

The apparatus may further comprise light waveguides embedded in the substrate.

The light waveguides may terminate in the transducers.

The light waveguides may terminate in the substrate outside of the transducers.

The apparatus may further comprise: (i) a wireless transmitter communicatively coupled to the transducers; and (ii) a battery electrically coupled to the wireless transmitter and to the transducers, wherein the wireless transmitter is configured to wirelessly transmit ultrasound data obtained using the transducers to a controller.

According to another aspect, there are provided various uses of the aforementioned apparatus. Namely, there are provided the use of the aforementioned apparatus for structural integrity testing, pipeline monitoring, hydraulic testing, aircraft wing non-destructive testing, a medical diagnostic, performing an ultrasound of a breast while a mammography is being performed on the breast, one or both of chemical and biological testing, heart monitoring, blood pressure monitoring, performing a transcranial ultrasound, cleaning debris such as one or more of dirt, dust, water, ice, and blood, and, for aspects in which the apparatus is transparent to x-rays, for generating an ultrasonic signal while an x-ray image is obtained through the apparatus.

According to another aspect, there is provided a mammography scanning system comprising: (i) a top compression device and a bottom compression device, wherein a space between the top and bottom compression devices is for receiving a breast; (ii) an x-ray emitter positioned to irradiate the space between the compression devices with x-rays; (iii) an x-ray receiver positioned to receive the x-rays after passing through the space; and (iv) any of the foregoing aspects of the apparatus transparent to x-rays positioned between the x-ray emitter and the x-ray receiver.

The apparatus may be positioned adjacent to or within one of the compression devices.

The array may non-uniformly attenuate the x-rays when in use, and the apparatus may further comprise a compensation device positioned between the x-ray emitter and the x-ray receiver and along a trajectory along which the x-rays travel. The compensation device may comprise an x-ray absorbing material of varying thickness across the compensation device such that the apparatus and the compensation device collectively uniformly attenuate the x-rays passing through the array.

The apparatus may have a wider field of view than the x-ray emitter and receiver.

The field of view of the apparatus may include a chest wall behind the breast.

According to another aspect, there is provided a flexible capacitive micromachined ultrasonic transducer array or fabric that can conformally cover a variety of surfaces, including but not limited to: flat and curved surfaces, surfaces with irregular shapes, spherical and cylindrical surfaces (such as pipes and tubes).

According to another aspect, there is provided a method of fabricating polymer-based capacitive ultrasonic transducers on flexible substrates. This fabrication methodology employs the benefits of a polymer materials such as inexpensive, easy to process and being capable of being made in large arrays.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIG. 19 is a screen shot from a simulation result when a theoretical breast was compressed against a poly-CMUT ultrasound array with walls measuring 60 μm by 100 μm in height;

FIG. 20 is a screen shot from an FEM simulation result when a theoretical breast was compressed against a poly-CMUT ultrasound array with walls measuring 70 μm by 100 μm in height;

FIG. 21 is a screen shot from an FEM simulation result when a theoretical breast was compressed against a poly-CMUT ultrasound array with walls measuring 50 μm by 250 μm in height;

DETAILED DESCRIPTION

Figure 1A:
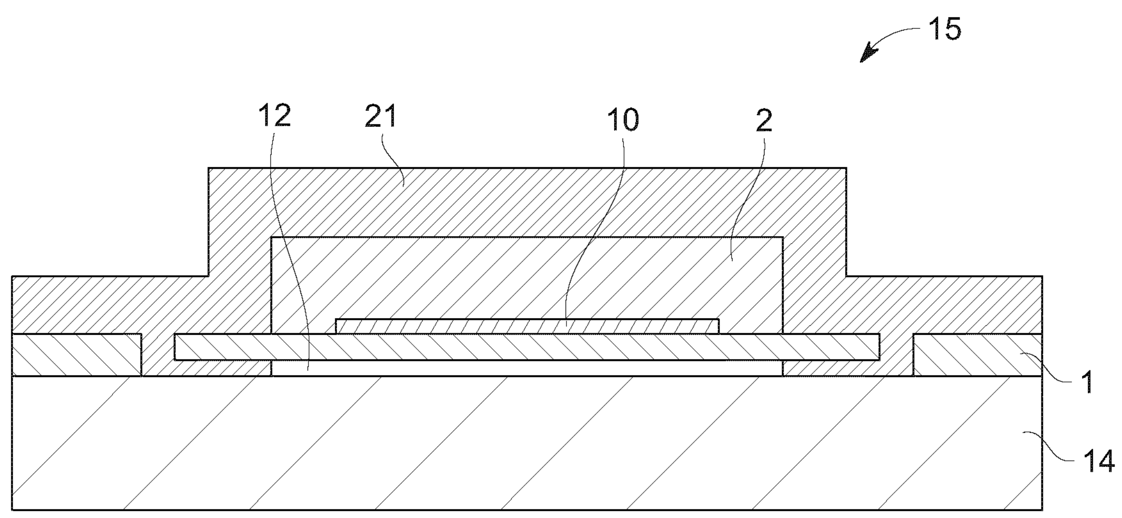
FIG. 1A is a line drawing illustrating a single polymer-based capacitive micromachined ultrasonic transducer element ("poly-CMUT") in a cross section showing the component parts.

The following terms are defined below.

The term "Polymer-based Capacitive Micromachined Ultrasonic Transducer" (poly-CMUT) is intended to mean a layered ultrasonic device with polymeric membrane containing an embedded upper electrode suspended above a cavity. Examples of a poly-CMUT are found in U.S. Pat. No. 10,598,362 by Gerardo, Rohling and Cretu. Examples of poly-CMUT structures are found in FIG. 1A (cross section), FIG. 1B (top plan of same structure), FIG. 1C (cross section of another embodiment) and FIG. 1D (top plan of embodiment of FIG. 1C). In contrast to conventional CMUTs, in the poly-CMUT, the top electrode is embedded within two polymer layers, with the bottom layer being thinner than the top layer. Combined with forming a sufficiently thin CMUT cavity, this structure permits the CMUT to reach the MHz operative region without requiring unacceptably high operating voltages. "Poly-CMUT" elements may be formed by the methods disclosed in U.S. Pat. No. 10,598,362 by Cretu et al. or U.S. Pat. No. 7,673,375 by Chang et al. An illustration of a poly-CMUT appears in FIG. 1A, at 15, with electrode 10, first polymer layer 1, second polymeric layer 2, a cavity 12, and substrate or base 14.

Used in the manufacture of the poly-CMUTs are OmniCoat™ composition (Kayaku Advanced Materials, Inc., Westborough, MA) comprises cyclopentanone solvent, propylene glycol monomethyl ether (PGME), a polymer and a surfactant (each less than 1 percent of total volume); LOR™ (Lift-off resists) composition (Kayaku) is made of cyclopentanone, PGME, a polyaliphatic imide copolymer, and a proprietary dye (less than 2 percent of total volume) and a surfactant; and "SU-8", an optically transparent polymer-based photoresist material that comprises bisphenol A Novolac™ epoxy dissolved in an organic solvent and comprises up to 10 weight percent triarylsulfonium/hexafluoroantimonate salt (Kayaku).

As used herein, "embedding" an electrode within a polymer layer means completely covering the electrode with the polymer, except for any electrical connections made with that electrode. These connections are formed before completely embedding the electrode within a polymer layer.

Also as used herein, "patterning" a material means to selectively remove that material either directly (e.g., if it is photosensitive) or by using a masking layer (e.g., in the case of the OmniCoat™ or LOR™ composition).

The sacrificial layer used can be directly deposited on flat or curved surfaces using spin or spray coating with a very controllable thickness. The nature of this (also polymer-based) sacrificial layer allows for much more flexibility in the fabrication process. Compared to silicon-based CMUTs, their sacrificial layer can only be deposited or growth in high-temperature chambers above selected substrates.

"Substrate" means an underlying substance or layer upon which the poly-CMUTs devices are fabricated. Substrates can comprise a range of metallic (e.g., aluminum), non-metallic (e.g., ceramics, composite materials), semiconductors (e.g., silicon) and even polymer-based materials such as polyimide, Kapton™, plexiglass or Lexan™. A substrate can also comprise optically transparent or semitransparent materials such as glass or Indium Tin Oxide (ITO). A substrate can be rigid, semi-rigid or flexible. A substrate can also comprise combinations of the aforementioned options, for example, a piece of glass covered by a layer of indium tin oxide, or a piece of polyimide covered by a metallic layer.

As used herein "fabric" or "array" is intended to mean a linear (1-D array), rows of linear arrays (1.5D array) or two-dimensional array (2-D array) of poly-CMUT elements in communication with each other and capable of communication with user interfaces either by wired communication or wireless signals.

"Low power" or "passive power" is intended to mean wireless power transfer using electromagnetic fields performed at a frequency that matches the resonant frequency of the poly-CMUT transducers. Exemplary frequencies are the so-called radiofrequency range, including Very Low Frequency (VLF) from 330 kHz, Low Frequency (LF) from 30-300 kHz, Medium Frequency (MF) from 300 kHz-3 MHz, High Frequency (HF) from 3-30 MHz, Very High Frequency (VHF) from 30-300 MHz, and Ultra High Frequency (UHF) from 300 MHz-3 GHz. The high MHz to low GHz range includes cellular, Bluetooth™ and WiFi™ frequencies so it is possible to perform wireless power transfer with those technologies. It is also possible to include a frequency converter to convert between the frequency of the wireless power transfer and the resonant frequency of the poly-CMUT transducers that emit ultrasound near the resonant frequency into the medium.

Figure 2A:
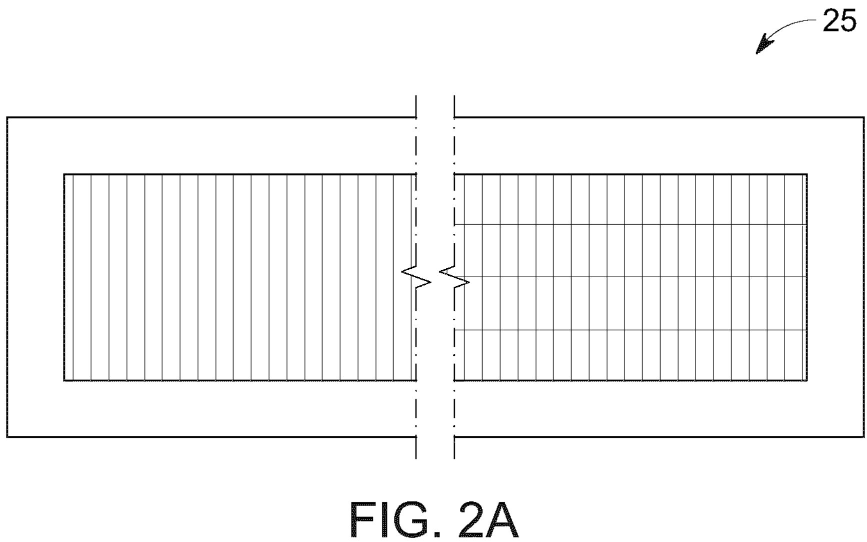
FIG. 2A is a line drawing of two possible organizational patterns of electrical connections among poly-CMUTs to form fabric, linear in side-by-side orientation (1.5 D) on the left, and 2-D array (2D) on the right.
Figure 2B:
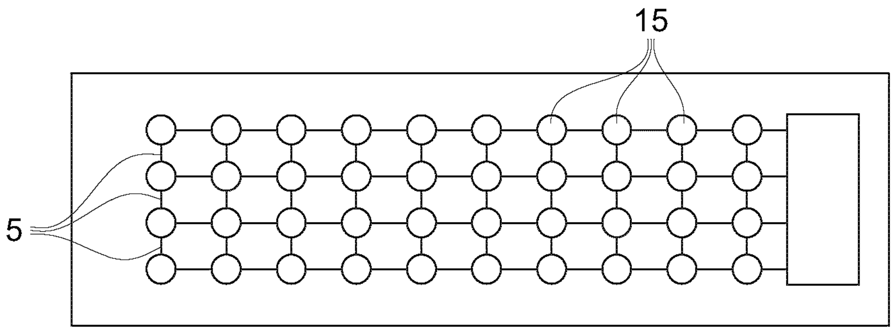
FIG. 2B is a line drawing of a 2D poly-CMUT array, with individual poly-CMUT cells depicted as circles in parallel connection with each other.
Figure 2C:
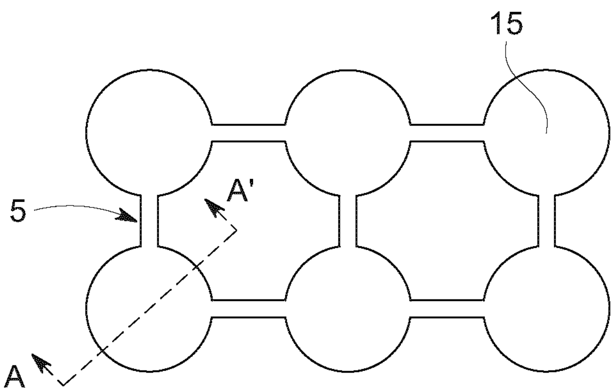
FIG. 2C is an enlargement of a small section of FIG. 2B, showing in detail how individual cells are connected in parallel using a common electrode.

As used herein "array" is intended to mean a group of poly-CMUT elements aligned side by side in a one-dimensional (1-D) arrangement, multiple linear arrays located side by side (1.5-D) or two-dimensional array (2-D array, often called matrix array) of poly-CMUT elements in communication with each other and capable of communication (once connected or active) with user interfaces either by wired communication or wireless signals. FIG. 2A illustrates a 1D array of poly-CMUTs 15 with vertical lines of poly-CMUTs on the viewer's left hand side, and a 2-D array on the viewer's right hand side of the image. FIG. 2B is a magnification of a layout with a series of four linear strips of poly-CMUTs on substrate 14. A more detailed 2-D array is shown in FIG. 2C, in which poly-CMUTS 15 are in communication with each other via electrical connectors 5. An x-ray transparent array is referred to in FIG. 12C at 40.

X-ray mammography means the practice of using radiographic imaging of a breast of a patient to screen for breast cancer. Young women in particular have a high proportion of dense breast tissue. During the radiographic imaging, the dense breast tissue absorbs X-radiation in a manner which is to some extent similar to potential tumor tissue, making it difficult to distinguish between dense breast tissue and potential tumor tissue. Poly-CMUT arrays are useful in association with x-ray mammography.

"Pillar" is a structure proximal to the poly-CMUT and which protects the poly-CMUT from direct contact by impinging bodies. Pillars are indicated in the images by number 16.

Photoacoustic (PA) imaging is a biomedical imaging modality in which nonionizing laser pulses are delivered into biological tissues. Some of the delivered energy will be absorbed and converted into heat, leading to transient thermoelastic expansion and thus wideband (i.e., MHz) ultrasonic emission. Typical reception frequency responses of classical piezoelectric (PZT) ultrasonic imaging transducers, based on PZT technology, are not sufficiently broadband to fully preserve the entire information contained in PA signals. CMUTs exhibit both higher sensitivity and significantly broader frequency response in reception, making them more effective in association with PA imaging applications than PZT ultrasound.

Elastography is a medical imaging modality that maps the elastic properties and stiffness of soft tissue. The main idea is that whether the tissue is hard or soft will give diagnostic information about the presence or status of disease. For example, cancerous tumors will often be harder than the surrounding tissue, and diseased livers are stiffer than healthy ones. Poly-CMUT arrays are useful in association with elastographic devices, particularly in comparison with PZT ultrasound.

Magnetic resonance imaging (MRI) is a medical imaging technique used in radiology to form pictures of the anatomy and the physiological processes of the body. MRI scanners use strong magnetic fields, magnetic field gradients, and radio waves to generate images of the organs in the body. MRI does not involve x-rays or the use of ionizing radiation, which distinguishes it from CT or CAT scans and PET scans. Poly-CMUT arrays are useful in association with MRI scanners, particularly in comparison with PZT ultrasound.

Figure 7:
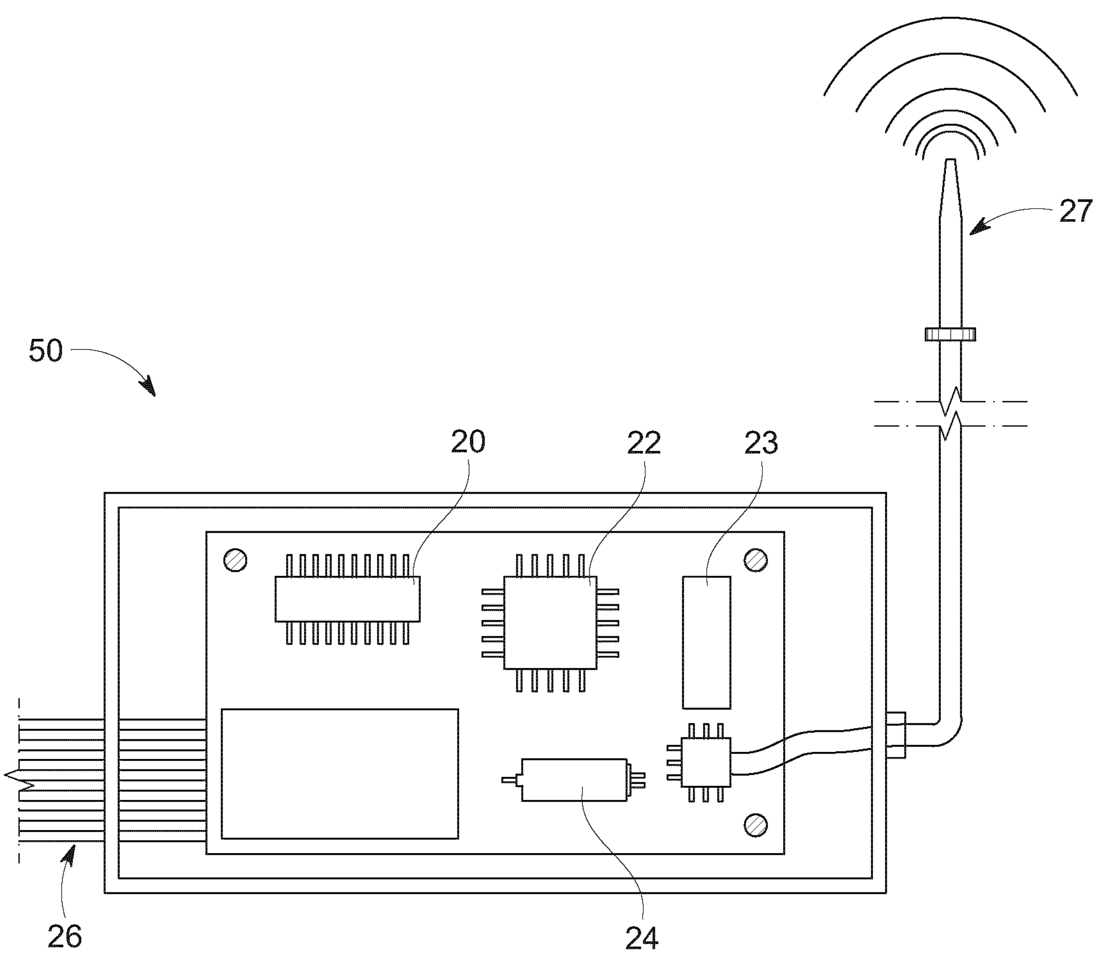
FIG. 7 is a line drawing of a generic ultrasound control panel which includes a processer, a beam former, an analog front-end electronic components, a battery, a manifold for receiving the wired connections from multiple CMUT elements, and an antenna, among other parts not shown.
Figure 9A:
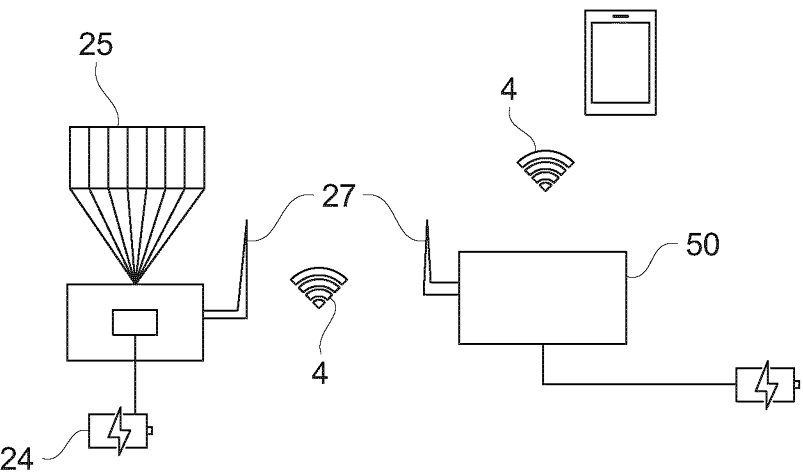
FIG. 9A is a schematic of a poly-CMUT patch, power sources and controls according to one embodiment.
Figure 9B:
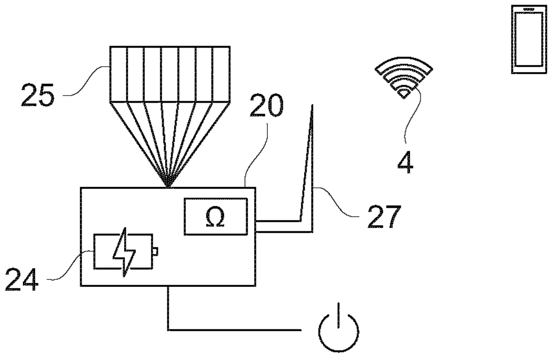
FIG. 9B is a schematic of a poly-CMUT patch, power sources and controls according to another embodiment.
Figure 9C:
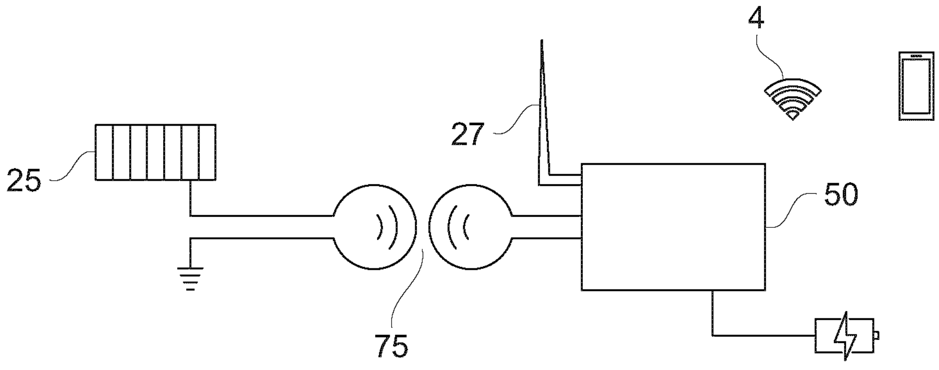
FIG. 9C is a schematic of a poly-CMUT patch, power sources and controls according to yet another embodiment.
Figure 26:
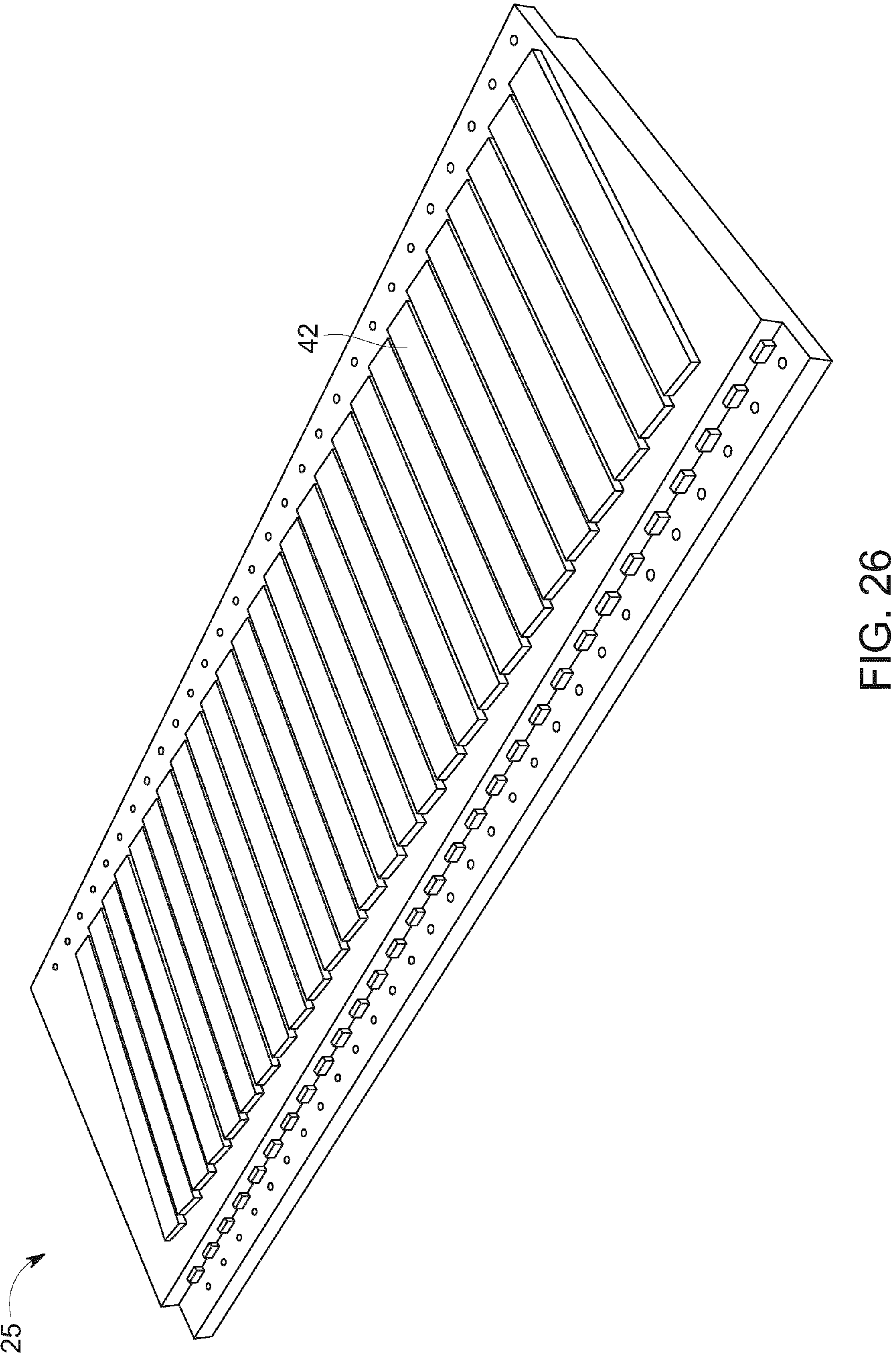
FIG. 26 shows an alternate perspective view of a section of a flexible poly-CMUT array from the other direction, again with poly-CMUT elements located at the top.

As used herein "wearable poly-CMUT patch" is intended to mean a linear (ribbon form, 1-D), a series of ribbon forms (1.5D) or 2-dimensional array of poly-CMUT elements (2-D) connected to transmit and receive electronic signals either by wired communication or wireless communication from controller 50, for example as indicated in FIGS. 9A, 9B and 9C. The transmission and reception electronics are connected to a controller connected with the array(s) by either wired communication as shown in FIG. 7 26, or wireless communication 75 as shown in FIG. 9C.

As used herein "transparent" is intended to mean that a portion of the electromagnetic spectrum (including x-rays, ultraviolet, visible light and infrared light) or other form of energy that can travel though a material without significant attenuation. For instance, the photopolymer SU8 allows close to 97% of light (from 400 nm to 800 nm and above) to pass through films. In reference to x-ray transparency, Table 1 compares absorption percentages for different materials where a 1000 μm-thick substrate made out of Polyimide can be considered x-ray transparent compared to Lead or to Silicon.

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.). In this disclosure the singular forms an "an", and "the" include plural referents unless the content clearly dictates otherwise. Thus, for example, reference to a composition containing "a compound" includes a mixture of two or more compounds.

In this disclosure term "or" is generally employed in its sense including "and/or" unless the content clearly dictates otherwise.

1 is the first polymer-based layer.
2 is the second polymer-based layer.
3 is ultrasound.
4 is a wireless communication.
5 is an electrical connection between and among poly-CMUT transducers.
7 is a monitoring vehicle.
10 is the top electrode sandwiched between the first polymer layer 1 and the second polymer-based layer 2.
12 is the cavity of the poly-CMUT cell.
14 is a substrate.
15 is an individual poly-CMUT cell.
16 is a pillar/protective wall.
17 is a second polymer-based layer.
18 is a first polymer-based layer.
19 is a brace or fastener.
20 is a microprocessor.
21 is a protective polymer coating.
22 is a beam former.
23 is a memory.
24 is a battery.
25 is a poly-CMUT array or element comprising several arrays.
26 is a wiring out to the poly-CMUT arrays or elements.
27 is an antenna.
29 is any pipe.
30 is a mammography scanning system.
31 is a mammography structural support device.
32 is a mammography bottom compression device.
33 is a mammography top compression device.
34 is an x-ray emitter.
35 is an x-ray detector.
37 is an external optical waveguide.
38 is an external optical light source.
39 is a combination x-ray ultrasound.
40 is an x-ray transparent poly-CMUT system.
41 is a transparent poly-CMUT ultrasound array.
42 is an individual linear array (1D).
44 is a fiducial marker.
46 is an outline of a focused ultrasound beam from a linear array.
47 is an outline of a focused ultrasound beam from a matrix array.
48 is an increased field of view of an ultrasound image due to beam steering.
50 is a controller/transmitter/receiver.
60 is a compensation device. It is used in case the poly-CMUT array 41 is not completely x-ray transparent.
61 is the substrate of the compensation device (should be x-ray transparent such as carbon fiber or polyimide).
62 is an absorbing material with specific heights that can be used to "correct" the total attenuation of the poly-CMUT array across the different paths.
64 is a main waveguide or a manifold of waveguides to transmit light from a light source, e.g., an optic fiber.
65 is an internal waveguide to distribute the laser pulses between poly-CMUT elements or cells.

66 is an output of these waveguides 65 that are located underneath of poly-CMUT cells or elements.

75 is a passive powering interface.

91 is an ultrasound coupling gel.

A is a human breast or model thereof.

Z' to Z" is a trajectory of a steered ultrasound beam.

101 is an electrical connection point or via.

102 is a mechanical cavity or receptacle for joining arrays together, see 104.

103 is an electrical connection point or via.

104 is a mechanical protrusion sized to frictionally fit cavity 102.

In this context, at least some embodiments of the present invention focus on specific specializations of poly-CMUT technology for non-destructive testing of physical structures as well as clinical purposes.

Size, weight, rigidity, fragility, and power transfer capabilities and needs of traditional ultrasound transducers further limit their performance for use in "non-destructive (structure) testing" (NDT) of metallic and composite materials, as well as in healthcare applications involving human tissue.

Referring now to the drawings, and more particularly to FIG. 1A, a line drawing illustrates the basic structure of a poly-CMUT 15. The substrate 14 is composed of a metallic substrate, polysilicon, or more preferably a silicon wafer. The polymer layer 2 over the electrode 10 covers cavity 12. Protective polymer overcoating 21 is shown sealing the whole cell.

Figure 1B:
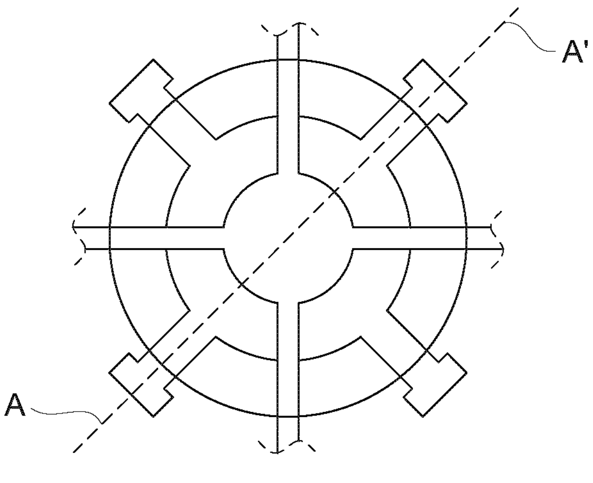
FIG. 1B depicts the cross-sectional view A-A' from FIG. 1A showing the topography of the different building layers.

FIG. 1B depicts the top view of a poly-CMUT cell according to the methods disclosed in United States Patent Publication No. 2019187101 by Cretu et al and placed here for clarity purposes.

Figure 1C:
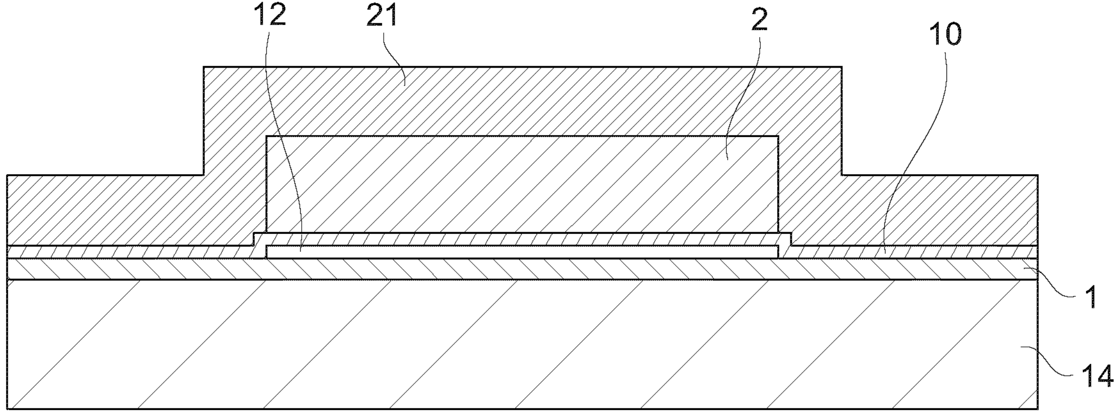
FIG. 1C depicts the cross-sectional view A-A' from FIG. 1B showing the topography of the different building layers. The top electrode is not embedded and is located right above the sacrificial layer. A sharp height transition of the top electrode is highlighted.
Figure 1D:
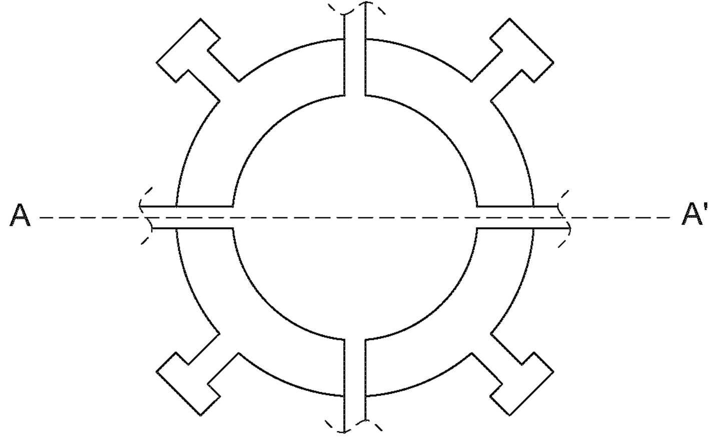
FIG. 1D depicts the top view of a poly-CMUT cell according to a second embodiment.

FIG. 1C depicts the cross-sectional view A-A' from FIG. 1D showing the topography of the different building layers. The sealed cavity 12 is achieved after etching the sacrificial layer by the methods described in in United States Patent Publication No. 2019187101 by Cretu et al.

FIG. 1D depicts the top view of a poly-CMUT cell according to a second embodiment of this document, where the order of the fabrication process is altered. The top electrode 10 is not embedded between the first polymer-based layer 1 and second polymer-based layer 2, but it is rather located right above the cavity 12.

Figure 15:
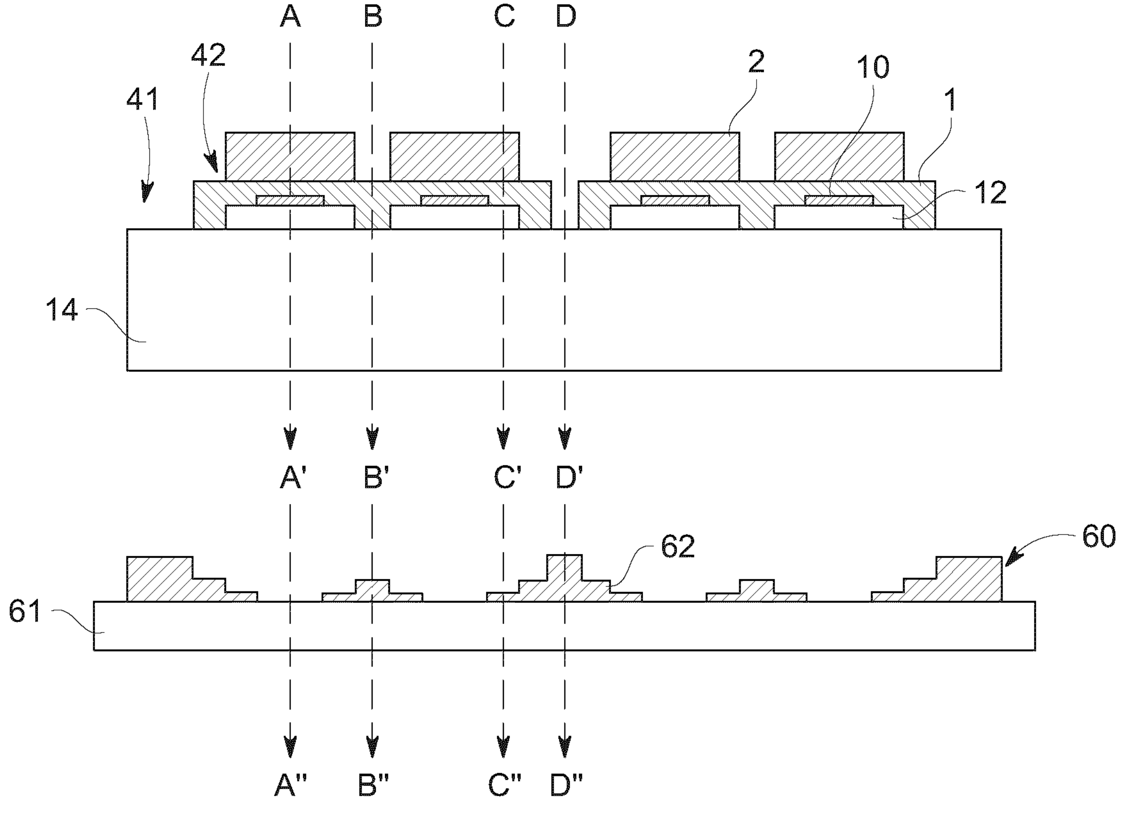
FIG. 15 shows the cross-sectional view of a transparent ultrasound array showing several poly-CMUT cells and a compensating layer optionally used in association with the transparent ultrasound array.

Power. Electrical charges trapped in the membrane act as a built-in DC bias. Poly-CMUTs can be used as a passive device (no external power) during reception. Alternately, low excitation voltages are required ($10V_{DC}+12\ V_{AC}$). This contrasts with high voltages (>50V) required by CMUTs or piezoelectric-based transducers to operate. As used herein "poly-CMUT array" is simplified in FIG. 2A to show a linear array (ribbon form), side-by side ribbon array form (1.5D) and a 2-dimensional array form of poly-CMUT. Any one of these forms may be labeled as 25 in the drawings. As illustrated in FIG. 2B and FIG. 2C, poly-CMUT cells 15 are connected to other cells via connectors 5. The transmission and reception electronics are then connected to a controller connected with the array(s) by either wired communication or wireless communication as exemplified in schematics such as those shown in FIGS. 9A to 9C. In FIG. 15, the x-ray transparent poly-CMUT array 41 is used to acquire an ultrasound image in the presence of x-rays. A compensation device 60 (shown in FIG. 15B) is mounted (or glued) right under the array 41 so that the overall path of the x-rays across the trajectories A-A'-A", B-B'-B", C-C'-C" and D-D'-D" have the same x-ray attenuation and the array 41 appears uniformly x-ray transparent in the final X-ray image.

Wireless communication also includes wireless power transfer in some embodiments, wherein a transmitter device, for example shown in FIG. 9C at 75, driven by electric power from a power source, generates a time-variant electromagnetic field, which transmits power across a space 75 to a receiver device, which extracts power from the field and provides it to an electrical load. Examples of wireless power transfer include inductive coupling, resonant inductive coupling, capacitive coupling, magnetodynamic coupling, microwaves, and light waves. The coupling can be nearfield coupling or intermediate coupling. These are all electromagnetic energy. Frequency can be kilohertz to megahertz waves, microwaves, x-rays, and light waves (solar power and lasers). Such waves can be produced by antenna or other coupling devices. This includes electromagnetic energy from simultaneous magnetic resonance imaging or x-ray imaging. Other examples are from kinetic energy from acoustic waves and surface waves, and thermal energy from heat. The coupler can be attached externally to the poly-CMUT transducer, as shown, or embedded directly in the poly-CMUT transducer elements. The advantage of using wireless power transfer is to increase convenience and safety, and reduce the size, weight, cost, and complexity of the wearable poly-CMUT patch. An example application is a lightweight patch that is unobtrusive to the wearer. Another example application is an embedded or implanted patch in which wires would be prohibited because of concerns about infection.

Figure 3A:
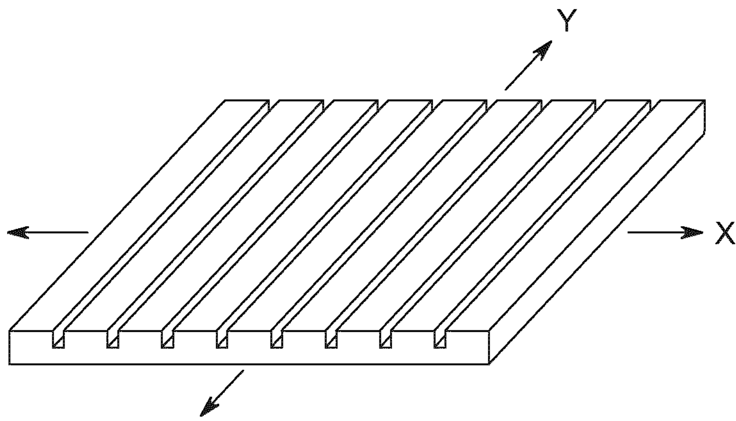
FIG. 3A is a model of poly-CMUT fabric with structural allowances for flexibility in one dimension.
Figure 3B:
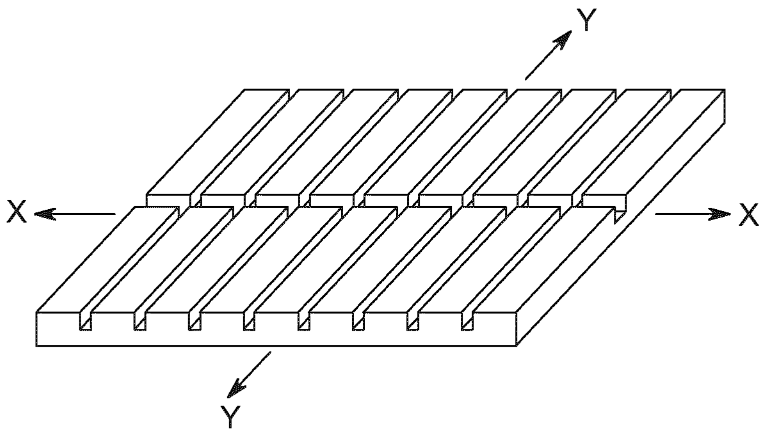
FIG. 3B is a model of poly-CMUT fabric with structural allowances for flexibility in two dimensions.
Figure 4A:
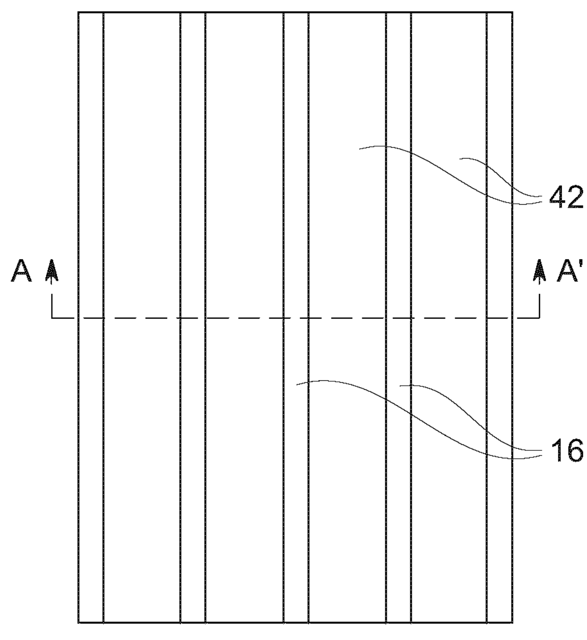
FIG. 4A is a line drawing of an embodiment of the poly-CMUT array wherein structural blunt-ended elevations protect the CMUT panels in the "valleys" between. Note that no poly-CMUTS are shown.

Advantages. Poly-CMUTs have numerous advantages over traditional silicon based CMUTS. For example, the total manufacturing cost of poly-CMUTs is estimated to be well below $100 unless the polymer is more expensive, or the electrodes are a high value metal like gold. Minimal and inexpensive manufacturing equipment are required for poly-CMUTs (mask aligner, metal evaporator, critical point drier). This is an advantage over silicon-based CMUTs, where expensive and cumbersome equipment is needed. The poly-CMUT arrays of at least some embodiments of the invention also possess flexibility as shown in arrays in FIGS. 3A and 3B, showing bendability in either one (x) or two (x, y) dimension because of break in the pillars 16 for wrapping around 3 dimensional shapes, and, as illustrated in FIG. 4A, cross section 4B, and perspective view 4C, protective pillars 16 to allow contact with surfaces without impinging on the ultrasonic capacity of the poly-CMUTs. FIG. 4A shows the top and cross-section al view of a linear poly-CMUT array with protective walls guarding the channels populated by poly-CMUT arrays 42. The protective barriers 16 can have different forms and sizes. A rectangular wall is shown in this figure, but more complex shape like a zig-zag format wall could be used to increase the mechanical robustness of the structure. Curvilinear walls are useful in some embodiments.

Polymer-based CMUTs can be manufactured on flexible substrates for wearable applications. This cannot be done with silicon-based CMUTs since they need rigid substrates, and this is absolutely not possible with ceramic piezoelectric materials.

Manufacturing polymer-based CMUTs can be theoretically scaled up to roll-to-roll fabrication, decreasing the manufacturing costs even further.

Manufacture of the poly-CMUT component array

An OmniCoat™ composition is used for a sacrificial layer in manufacture. Other possible choices include LOR™ or even metals compatible with the chemicals and materials used in fabrication.

A photoresist such as S1813 or SU-8 (purchased from Kayaku) is deposited on top of the sacrificial layer. The photoresist layer is then exposed to UV after placement of a photomask and mask aligner, and the uncrosslinked photoresist is removed using an aqueous solution containing an alkaline-based photoresist developer (MF319 or any similar TMAH-based developer).

The masking layer of positive photoresist is then removed by immersing the sample in acetone or any other solvent suitable to dissolve it without damaging the sacrificial layer.

What is left behind is a patterned sacrificial layer containing the areas that will become the cavity 12 in the final device as well as the etch channels.

SU-8 photoresist is then used to cover the sacrificial layer. The thickness of the layer is as thin as possible to conformally coat the sacrificial layer and to maintain good electrical insulation between the conductive substrate, which acts at the finished CMUT's bottom electrode, and a top electrode.

In different embodiments, the polymer-based material may have a different composition. In at least some different embodiments, a material may be used in place of the SU-8, and that replacement material may be partially or entirely transparent, such as polydimethylsiloxane (PDMS) or polymethyl methacrylate (PMMA) photoresist. These polymer-based materials can also be treated to modify their optical or mechanical properties; for instance, a color-specific dye can be added to filter certain light wavelengths for combined diagnostic instruments, or metal or magnetic fillers (e.g., silver nanowires, gold nanoparticles, carbon nanotubes, etc.) can be added to modify their electrical, mechanical, thermal or magnetic properties. In other embodiments, the poly-CMUT is prepared in a wafer-bonding technique.

An electrically conductive top electrode (chromium or other metals such as gold or aluminum) is patterned on top of the cross-linked areas of the first polymer-based layer as shown in FIG. 1A at 10. The top electrode can be any other material capable of fulfilling the functions of the top electrode can be used (e.g., conductive polymers such as PEDOT:

PSS, optically transparent materials such as Indium Tin Oxide, etc.). A good adhesion between this top electrode and the cross-linked areas is essential in order to avoid any potential delamination during normal operation of the finished device.

At this point the overall thickness of the membrane (i.e., the crosslinked areas and the top electrode) is thin compared to its diameter, so that its resonant frequency would be just a fraction of the desired operational frequency in the finished device, and so a second polymer-based layer 21 is deposited over the membrane, coating the sacrificial layer, the first polymer-based layer, and the top electrode. This layer is shown in FIG. 1A and FIG. 1C at 2, for example.

The second polymer-based layer is of the same photosensitive polymer (SU-8) as the first polymer-based layer in some embodiments, but in other embodiments, the layers comprise different polymers. The thickness of this second polymer-based layer is much greater than that of the cross-linked areas of the first polymer-based layer, specifically about five times as thick in some embodiments.

Following the same process as described above, the second polymer-based layer is exposed to UV using a photomask and a mask aligner. The areas exposed to UV light become cross-linked areas and the areas not exposed to UV are left intact (uncross-linked). The uncross-linked areas of the second polymer-based layer are etched away by placing the sample in an aqueous solution containing a negative photoresist developer (SU-8 developer). The cross-linked areas remain intact.

At this point, the top electrode becomes embedded between the cross-linked areas of the two polymer-based layers. The patterned sacrificial layer is removed.

Any electrical interconnections 5 must be installed at this point. Referring to FIG. 2A, there are three possible poly-CMUT array organization plans. The left side is a row of side by side linear arrays, either a 1D or a "1.5 D" array, comprised of poly-CMUT elements that have independent electrical connections at the edges. The right side of the image of FIG. 2A represents a two-dimension matrix embodiment, where independent electrical connections are located at the periphery. A linear array is a strip form, with head to tail connections only. In a separate embodiment, the electrical interconnections can also be at the back of the poly-CMUT elements, simplifying the wire routing.

As illustrated most simply in FIGS. 2B and 2C, the circular forms represent poly-CMUT cells 15, and the lines therebetween are parallel connections 5.

After the electrical connections 5 have been formed, the poly-CMUT array is encapsulated by a suitable coating such as parylene, illustrated in FIG. 1 at 2. This coating of encapsulating material conformally seals the entire poly-CMUT array inside a low pressure chamber; for example, at $P=1\times10^{-3}$ Torr to form a closed cavity, which is vacuum sealed and impermeable. Extra protective layers of protection are provided according to embodiments of the invention where necessary.

An alternative fabrication of poly-CMUTs involves placing the first polymer-based layer right above the bottom electrode 10 (FIG. 1C) to act as an electrical insulating layer. In this process, the sacrificial layer is then deposited and patterned to later become the cavity. Then the top electrode 10 (electrically conductive such as metals or conductive polymers) is deposited and patterned. The last step involves depositing and pattern a second polymer-based layer that covers the top electrode. This fabrication approach decreases the effective distance between electrodes compared to the case where the electrode is placed above the second polymer-based layer.

In this fabrication approach, a conformal deposition of the top electrode is needed (e.g., metal sputtering) to maintain electrical uniformity of the top electrode. Alternatively, the thickness of the top electrode should be at least 1.5 times the thickness of the sacrificial layer if directional deposition methods are used (e.g., metal evaporation). Now referring to FIG. 7, there is shown an embodiment of a control panel in the form of a printed circuit board (PCB) with microprocessor 20, beam former 22, memory 23, battery 24, and analog front-end electronic component. Hardwiring out to the poly-CMUT panels are depicted at 26. Antenna 27 transmits signal to the user interface (not shown) which will have a graphical component or simple pass/fail readout depending on the application.

The poly-CMUT array is controlled and sometimes powered by controller 50, a schematic of which appears as FIG. 7, and which component includes the microprocessor(s) 20, memory 23, battery 24 and any other power source, any manifolds for wire organization for connectors 26, antenna 27, relays, and circuits required for receiving, organizing, and transmitting signals from the poly-CMUT array fabric.

The electrical circuits on the board are similar in some embodiments to those of a traditional ultrasound machine, and include pulsers, memory 23, communication components, and beam formers 22 to add time delays to poly- CMUT arrays to create a focused ultrasound beam, and the analog front-end (AFE) electronics as needed. Electronic interface circuits are commercially available from Verasonics, US4US, Interson, and Texas Instruments Ultrasound, for example. Such circuits are responsible for the conversion of electrical signals into acoustic signals, acoustic echoes into electrical signals, processing of the electrical signals from one or more transducer elements, and processing of the electrical signals into measurements or images of the target material. For non-destructive testing, airborne applications and specialized medical applications, 1-D single-line real time measurements are possible with lower-cost hardware, such as Raspberry Pi. Preferred embodiments include a high-capacity battery 24 and a memory 22 to store the captured data at fixed intervals or continuously.

Figure 4B:
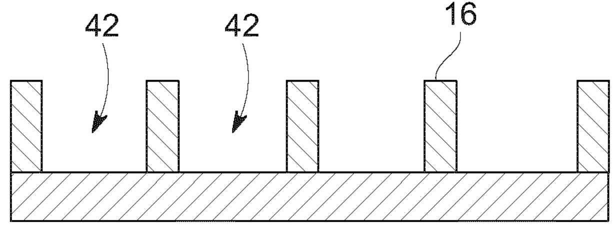
FIG. 4B is a cross sectional view of the line A-A' in FIG. 4A. Note that no poly-CMUTS are shown.
Figure 4C:
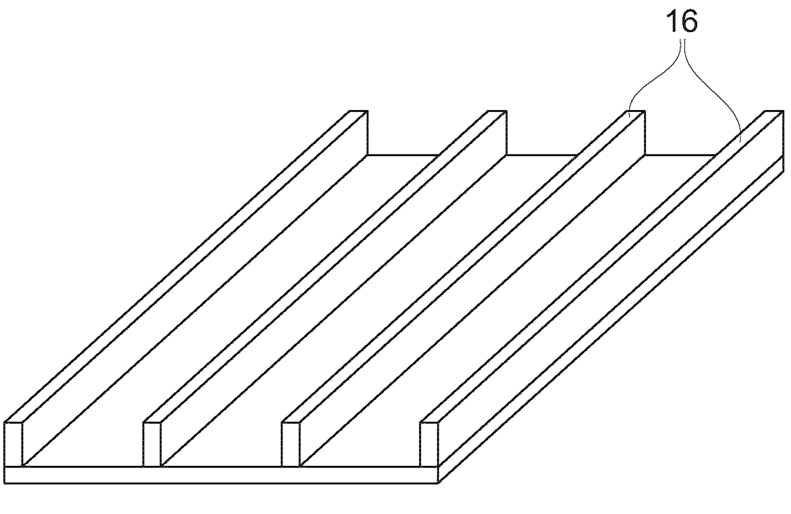
FIG. 4C is a perspective view of the line drawing of FIG. 4A. Note that no poly-CMUTS are shown.
Figure 10:
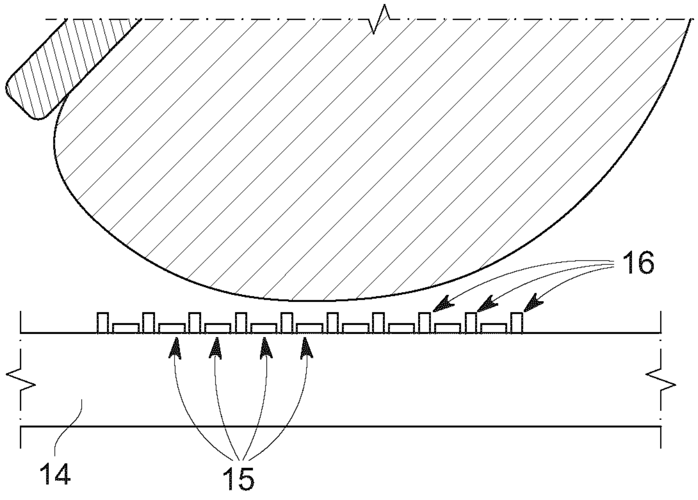
FIG. 10 is a line drawing of an embodiment of the CMUT fabric wherein structural blunt-ended elevations protect the CMUT panels in the "valleys" upon contact, with, say, human tissue.

Pillars. In embodiments of the invention, the poly-CMUT array is employed in an environment which requires protection of the membranes from the environment or surface of a target. The structure of such an array will include protective structures, herein called "pillars", which may be cylindrical, rectangular, circular, or wall-like, to prevent impingement on the poly-CMUTs. See FIGS. 4A, 4B an 4C showing protective pillars, and FIG. 10 showing a fingertip about to make contact with a poly-CMUT array protected by pillars 16. Observe that the poly-CMUT elements 15 project from substrate 14 in FIG. 10, but pillars 16 are more elevated than the CMUT elements, preventing direct contact. The minimum height for the pillars in some embodiments is greater than 50 μm in height. Pillars may be formed, in some embodiments, from one of the polymer layers. Pillars may support and contain conductive polymer gels over the poly-CMUT arrays.

The system of pillars or walls are dispersed within the poly-CMUT array in some embodiments, so that structural support against an applied external mechanical pressure is provided. In such a case, the transducers will only react to the acoustic pressure (generated by the echoes to the transmitted ultrasound), and be insensitive to the applied mechanical pressure. Pillars are necessary for instance in a using ultrasound imaging in a breast mammography system, for the breasts are being compressed with forces between 80-100N during such an examination, and such forces should not be exerted directly on the transducers.

One method of implementing such a system relies on tuning the fabrication technology, so that the SU-8 material used for fabricating the transducer membranes will have a supplementary layer deposition and patterning step. The extra step fabricates pillars or walls much higher than the membranes, and will support applied pressure including 80-100N.

A second method of implementing such system relies on using bonding techniques between two processed substrates. On the first substrate the poly-CMUT array is defined with the normal fabrication steps, exemplified in U.S. Pat. No. 10,509,013B2, 10,564, 132B2 and 10,598,632B1. On a separate substrate, a much thicker layer of SU-8 is being deposited and then patterned, for defining the pillars/walls pattern. The two modules are afterwards bonded together, face-to-face, and the substrate supporting the SU-8 pillars is removed.

The pillars/walls system provide protection from mechanical pressure, in that the external mechanical pressure is applied on the pillars/walls, and not directly on the very thin poly-CMUT membranes.

The pillars further provide decoupling between the mechanical and acoustic pressure systems, because the mechanical pressure is entirely supported by the pillars, the poly-CMUT cells sensitivity to the acoustic pressure is not affected by the external mechanical pressure, eliminating the cross-coupling between the two. In this way, the response of the probe is not affected by the pressure applied by the operator, for instance, when applying the probe on the body.

The pillars further reduce inter-cell cross-talk, depending on the specific design pattern of the pillars. One of the major challenges for CMUT arrays is the cross-talk between neighboring cells, because the vibrations of one cell, especially when actuated with stronger pulses, can transmit through the solid or the fluid environment, to neighboring cells, generating undesirable cross-talks. The pillars system creates an extra filtering obstacle for this inter-cell coupling, effectively reducing the cross-talk. The pillars further provide a support system for acoustic micro-lenses: the walls/pillars provide an extra space above the CMUT membranes that can be filled, through proper technology steps, with one or more layers of materials (e.g., PDMS) used to define acoustic micro-lenses, so that the energy of the acoustic wave is guided in a direction normal to the membrane. The pillars are part of the acoustic micro-lensing system, as they can act, depending on their height, as (partial) acoustic waveguides.

Assembly method by overlapping tape/patches. This is a general method of modular assembly for array of poly-CMUT cells disposed in regular patterns (one by two, two by four, four by four, and so on) on a flexible substrate. In this method, a flexible tape or patch serves as mechanical substrate for the fabrication of the array of the transducers on its top surface, while the bottom side can be specially treated in order to be adhesive. To ensure electrical interconnectivity between rows of cells fabricated on the top surface, each row has associated bondpads (electrical interconnect surfaces) at both margins of the patch/tape. A via mechanism, similar with the one used in fabricating flexible PCBs, connects the margin pads electrically to bottom margin bondpads patterned on the bottom surface of the tape/patch. The top and bottom sets of margin bondpads are aligned.

When the tape being made for wrapping a cylindrical surface such as a pipe of a defined circumference, the distance between consecutive rows of transducer cells (disposed transversally to the margin of the tape) is preferably made such that the diameter of the cylinder corresponds to an integer number of rows disposed around its circumference. The next tape wind will then align the next set of transducer rows with the previous ones, and provide electrical interconnectivity by overlapping the top margin bondpads of the previous tape with the bottom margin bondpads of the next wind of tape.

In a preferred embodiment, to ensure a better self-alignment, the tape structure has relief alignment lock-in patterns, such as trenches and wedges, for example, to enforce and stabilize the alignment of the connections among transducers.

In other embodiments, the alignment of bondpads described above is also used in flexible patches of various shapes and sizes, bands, foils, fabrics, and formed shapes of the poly-CMUT arrays.

Remote Control. The "Internet of Things or "IoT" describes devices that are connected to each other wirelessly. Power consumption is a major challenge because many IoT devices are battery powered and need to have a long lifetime in the field. A switched-off device reduces battery life but does not provide sensing when needed, so there is a need for an energy-efficient way to alert and turn on IoT devices. This means the devices need a wake-up receiver that can turn on/off the IoT devices. Ultrasound has several advantages for performing this task. It can use very small wavelength signals and therefore be much smaller than similar alarm receivers that use radio signals while operating at extremely low power and with a wider range. Such an ultrasound-based receiver listens for a small unique ultrasonic signal indicating when the device should be turned on. It has the potential to only require a nanowatt of signal power which is a tiny draw on valuable battery energy reserves. Moreover, the range of such ultrasound signals is naturally restricted, so it can be limited to inside a room for example, which has valuable privacy advantages. This concept can be extended beyond simple wake-up signals and include transmitting and receiving other information such as encoded passwords or other information. A further advantage is that the ultrasound frequencies do not interfere with the strictly controlled electromagnetic frequency ranges for IoT communications dictated by government controlled regulatory bodies.

Physical structures for the fabric of at least some embodiments of the invention are shown in FIGS. 3A and 3B. Rigidity is maintained by the substrate and pillars, but the fabric is flexible along the longitudinal axis or axes according to how the pillars 16 are arranged and whether the substrate 14 is supple.

Manufacture of poly-CMUT Foil. A poly-CMUT array can be fabricated on a metal substrate so that it behaves like a metal foil. Choices for the metal include aluminum, steel, copper or other metals. Such metal foils can be deformed from their originally manufactured shape into a new shape. The deformation can be limited to the elastic range and therefore return to the original shape when the deformation force is removed. This is useful when the poly-CMUT must be applied to one target material with a shape and then removed and applied to another target material with a different shape. The deformation can be plastic and retain the shape after the deformation force is removed. This is useful when the poly-CMUT must remain in place on a target material for an extended period of time.

Poly-CMUT Sleeve. A poly-CMUT array can be fabricated on a stretchable substrate in some embodiments so that it behaves like an elastic fabric. This is useful when a tight fit is needed between the poly-CMUT and the target material such as a sleeve on a pipe. For example, a tubular poly-CMUT can be stretched to a slightly larger diameter of the pipe, slid along the length of the pipe and then allowed to return to its original shape and conform closely to the pipe. This allows for ease of installation around a target material like a pipe. Alternatively, instead of behaving like an elastic fabric, the stretchable substrate behaves like heat-shrink tubing in some embodiments, wherein the application of heat results in a shrinkage of the substrate achieving the same goal of conforming closely to the target material. Other solutions known in the art can be used to allow ease the installation of a poly-CMUT sleeve on a target with a tight conformal fit. Manufacture of poly-CMUT Ribbon. A poly-CMUT can be fabricated on a stretchable substrate in some embodiments so that it can be wrapped tightly around a target material, like a pipe, so that it conforms closely without gaps.

Structural integrity testing. In still other embodiments, transparent poly-CMUTs array are used in non-destructive evaluation (NDT) of materials. Typically, x-ray imaging is used for inspection of materials, but the doses used contain a great percentage of ionizing radiation which in some cases produce internal damage to a test specimen. An x-ray transparent poly-CMUT array is used to obtain a hybrid image (ultrasound and x-rays) and potentially reduce the amount of x-ray energy needed. FIGS. 5A to 5E depict embodiments of the CMUT arrays in different formats for non-destructive structural testing of pipelines, aircraft hydraulics, or any kind of critical piping. For example, in NDT applications, the structure may be failing, and the graphical information about where the fault lies is optional depending on the user needs.

Pipeline Monitoring. A poly-CMUT array can be installed on a section of pipe at the time of placement of the pipe in the field in some embodiments. Alternatively, it can be installed on a section of pipe at the time of manufacture of the pipe to enable better integration with the pipe and protection of the poly-CMUT array from damage.

Hydraulics Testing. A poly-CMUT can be fabricated on a stretchable substrate in some embodiments, so that it can deform with the deformation of a hydraulic hose during normal operation.

Figure 5A:
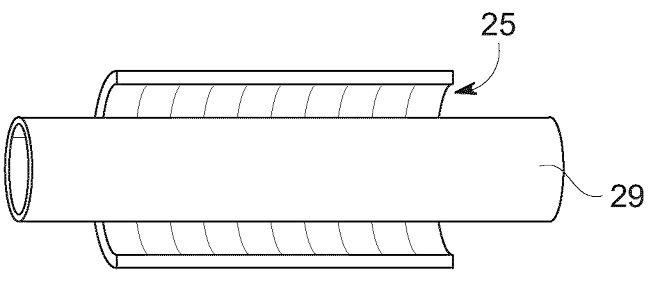
FIG. 5A is a line drawing of a pipe with the fabric according to one embodiment of the invention in an unwrapped form.
Figure 5B:
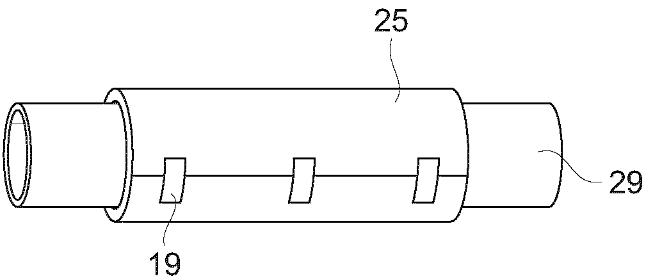
FIG. 5B is a line drawing of a pipe with the fabric according to one embodiment of the invention in a wrapped form.
Figure 5C:
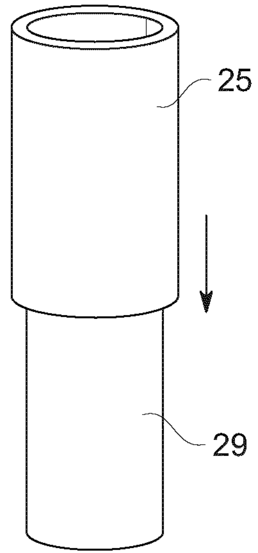
FIG. 5C is a line drawing of a pipe with a sleeve form of the fabric according to one embodiment of the invention.
Figure 5D:
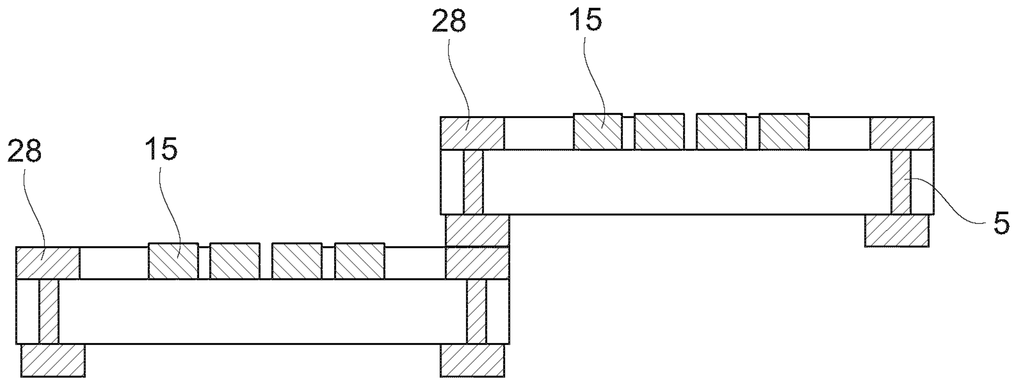
FIG. 5D is a line drawing of a stacked ribbon or linear form of poly-CMUT array, partially overlapping another, with bond pads and electrical connectors between the two elements, according to one embodiment of the invention.

FIG. 5A illustrates a 2-D array 25 in an open form of the array wrapped around a pipe 29 according to one embodiment of the invention. The same pipe is now wrapped with array 25 in FIG. 5B. The array 25 may be the form of a movable sleeve as illustrated in the embodiment shown in FIG. 5C, installed in any environment, either above ground, underground, or in a vehicle such as an aircraft. The array according to an embodiment of the invention may be linear or 2D in the form of a spooled ribbon, to wind a pipe 29 after the pipe has already been installed. The spooled ribbon connects to the next wind of ribbon, in some embodiments, by a system of bond pads such as those shown in FIG. 5D. In another form of connection, FIGS. 24 to 29 illustrate embodiments with mechanical connection cavities 102 and fitted protrusions 104, which mechanically connect the elements 25 to other elements 25 along their length. The electrical connections in the embodiment shown in FIG. 5D run through vias at 101 and 103.

Figure 5E:
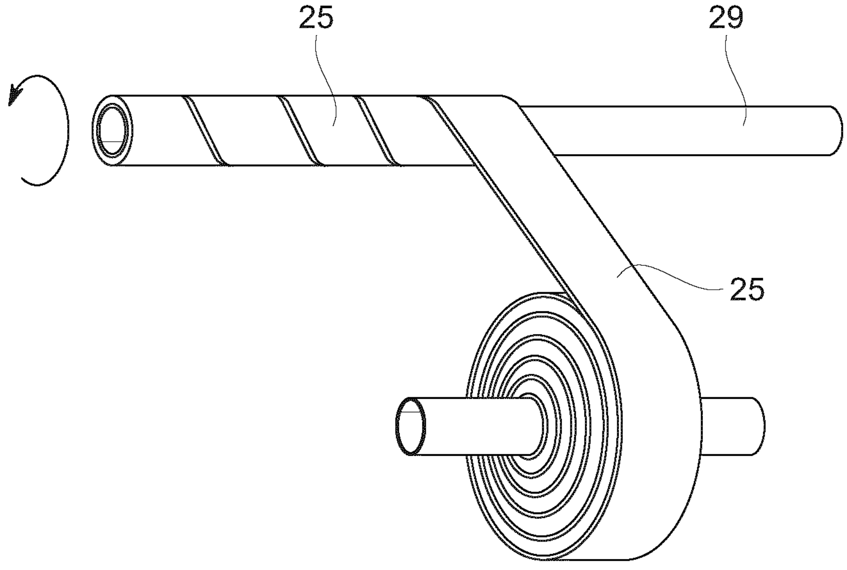
FIG. 5E is a line drawing of a pipe with a spooled ribbon form of the fabric according to one embodiment of the invention being used to wind a pipe.

FIG. 5E illustrates a ribbon form for the poly-CMUT fabric to be fabricated to wrap structures for NDT, this is especially useful to cover long pipes. The ribbon form may be stored in a roll that does not take up much space, so is transportable to any manner of location.

Electrical interconnections and flexibility of substrate will be customized depending on the diameter and length of the piping to be wrapped.

Figure 6A:
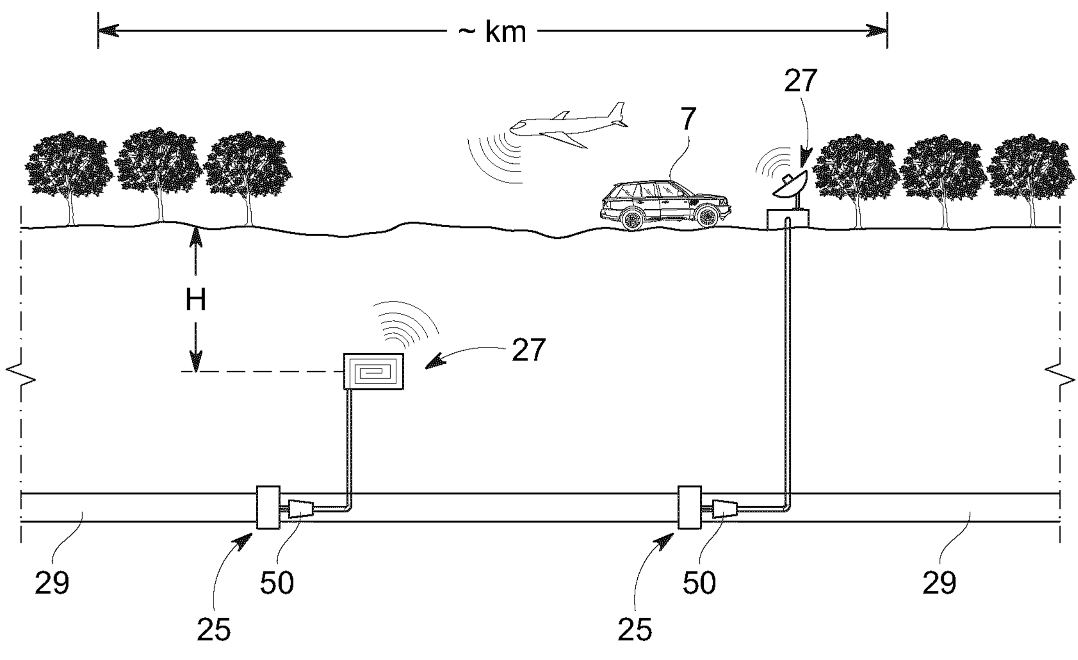
FIG. 6A is a sketch of the layout and surveillance of an underground pipeline fitted with periodic collar forms of the fabric according to embodiments of the invention.

Embodiments of the invention are useful for real time monitoring of pipelines underground in a form of "non-destructive testing" or "NDT". In FIG. 6A, a surveillance drone 7 his shown flying over buried pipe 29. A ground vehicle 7 such as a truck or car could also be used to monitor. Antenna 27 connected to the poly-CMUT array surrounding the pipe receives and sends signal to a reader in the drone, which is either recorded for later use or is transmitted live to a centralized monitoring station. In another embodiment, the antenna 27 is replaced or supplemented by a satellite antenna. Satellite transmissions are picked up by satellite and transmitted back to the monitoring station on ground level.

The pipe 29 shown in the ground has a partial poly-CMUT sleeve 25 connected to a controller 50, which is in turn connected to the antenna 27 which transmits data to observers above ground. In some embodiments, power is provided by the signal sent by the surveillance vehicle 7 or drone 7 (passive power) supplemented by the battery in controller 50. In other embodiments, a larger power source may be wired into the system.

Figure 6B:
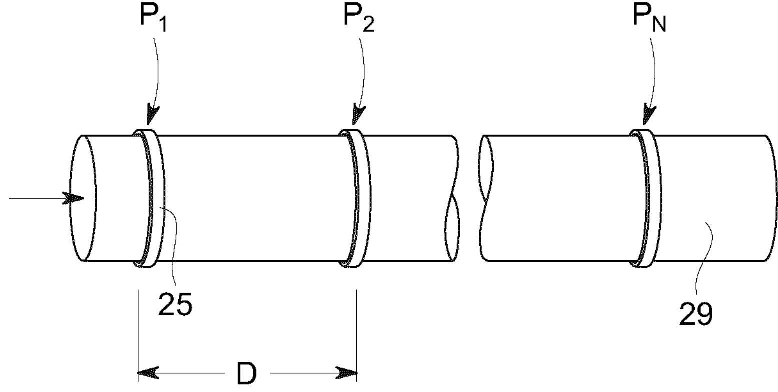
FIG. 6B is a line drawing of a pipe with periodic collar forms of the fabric at a distance D from each other. The arrow represents flow of liquid being transported by the pipe.

A closer look at a partially sleeved pipe as in FIG. 6A is shown in FIG. 6B. The pipe 29 may be above ground, in a building, or underground. Here, the partial sleeves 25 are a set distance apart. This arrangement is useful to measure the mechanical integrity of the pipe as well as the flow rate along the pipe (water, oil, gas), and any pressure differential among the data collection points which might indicate a crack or a leak.

Figure 8A:
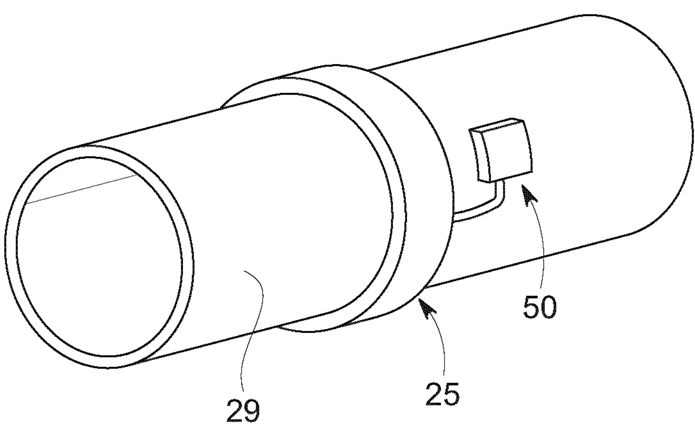
FIG. 8A is a line drawing of a section of pipe with a patch of poly-CMUT array according to one embodiment of the invention.

The poly-CMUT sensor array may also be used in partial covering for pipes, even two or more across the pipe 29 diameter as shown in FIG. 8A.

Figure 8B:
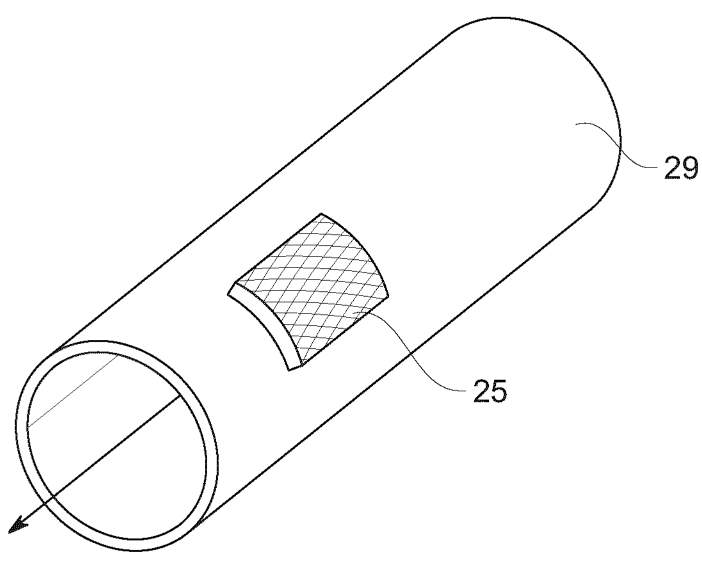
FIG. 8B is a line drawing of a pipe with a poly-CMUT array patch according to an embodiment of the invention.

A poly-CMUT sensor array suitable for a pipe 29 may also be in the form of a finite two-dimensional patch 32 such as the one shown in FIG. 8B.

Figure 8C:
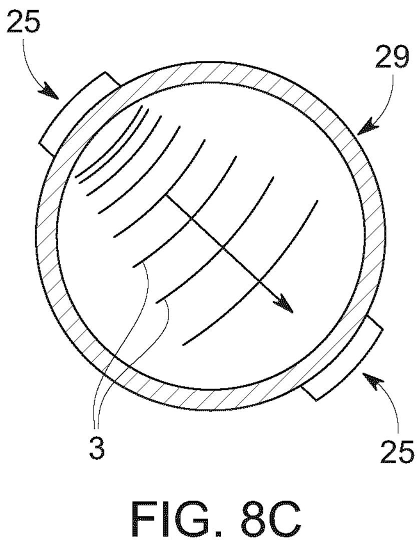
FIG. 8C is a line drawing of a cross section of a pipe with a patch of poly-CMUT array on opposite sides of said pipe, transmitting and receiving signals across the diameter of the pipe.
Figure 8D:
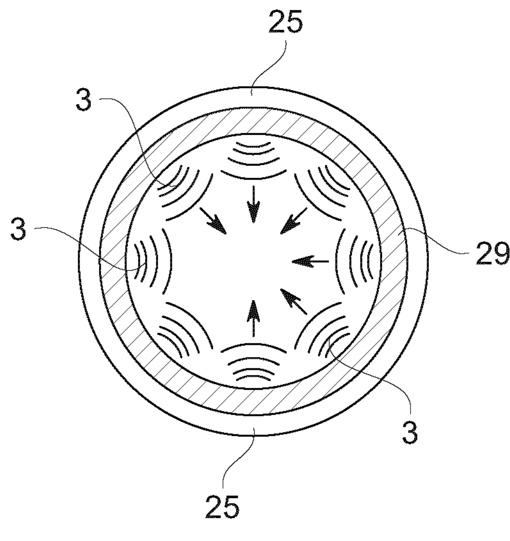
FIG. 8D is a line drawing of a cross section of a pipe with full wrapping of poly-CMUT array around said pipe, transmitting and receiving signals across the diameter of the pipe.

When the poly-CMUT array foil 30 is fully surrounding the pipe 29, the ultrasonic signal is present throughout the pipe subject to the power of the signal and the size of the pipe as shown in FIG. 8C. A close up of a cross section of a pipe fully wrapped in the poly-CMUT array fabric is shown in FIG. 8D.

Aircraft Wing NDT. The testing of large areas such as aircraft wings are difficult with small poly-CMUT. Even with larger poly-CMUT arrays, it would still take multiple fabric sheets to cover the entire wing. Although it is possible to move a poly-CMUT over all portions of the wing there are challenges of the speed of movement and the ability to maintain good contact with the wing at all times. In some embodiments, there is provided a rollable poly-CMUT array which can be installed around the perimeter of a wheel that can be rolled quickly over the wing. Operation would be analogous to a paint roller. The array stays on the roller. As one section of the wheel comes into contact with the wing, the poly-CMUT fabric portion that is in contact can perform ultrasound imaging. The speed of the movement of the wheel can be fast because the speed of ultrasound acquisition is high, ranging from 30 samples per second to more than 3000 samples to second. In order to make good contact between the poly-CMUT and the wing without air gaps, a source of fluid such as water or gel can be applied intermittently or continuously. An advantage of this operation is that the spacing of the poly-CMUT data acquisition is regular because it is determined by the spacing of the poly-CMUT elements on the wheel, not the speed of the movement of the wheel over the wing. The wheel can be rigid or deformable, where deformable products provides a larger contact spot on the wing. In an alternative embodiment, the poly-CMUT can be applied to a fabric that wraps around two or more wheels analogous to the tracks of a military tank, allowing a substantially flat portion of the poly-CMUT to come in contact with the wing at any given instance in time.

If large-scale poly-CMUT transducer arrays need to be used to inspect plane wings or other aircraft for instance, a large "foil" can be temporary attached to a wing for inspection.

A permanent monitoring solution would involve the transducers incorporated inside the fuselage to protect the transducers from physical wear and the elements.

Wearable poly-CMUT arrays. In another embodiment of the invention, the poly-CMUT array is employed on human or animal tissue. The flexible or rigid arrays thus formed for medical or agricultural applications is useful for providing information on injuries on site when an accident has occurred. Emergency responders can wrap the injured person in the fabric and 'see' the breaks and soft tissue injuries in the victim before initiating transport to medical care. This practice would include checking legs, arms, ribs and spine for breaks, and checking for impact injuries in the skull. In the form of wearable arrays shown in FIG. 11 at 25, low blood flow in certain locations may also be detected, indicating compression injuries. The structure of this array will include protective structures to prevent direct contact with the poly-CMUTS. The poly-CMUT elements 15 project from the substrate 14, but pillars 16 are more elevated than the CMUT elements, preventing direct contact and inhibition of the transducer function. For poly-CMUT array fabrication for human contact, after the electrical connections 5 have been formed, the poly-CMUT wafer is encapsulated by a bio-compatible material such as a poly(p-xylylene) polymer such as parylene, or polyvinylidene fluoride (PVDF), or silicone inside a low-pressure chamber to preserve low pressure in the enclosures (for example, $P=1\times10^{-3}$ Torr). The encapsulating material conformally seals the entire cell to form a closed cavity, which is vacuum sealed and impermeable.

Figure 13A:
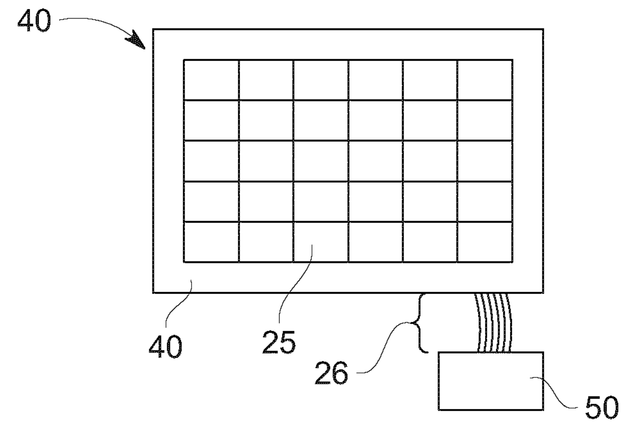
FIG. 13A depicts a transparent poly-CMUT system in the form of a matrix showing a transparent substrate, interconnection cables and a controller.
Figure 13B:
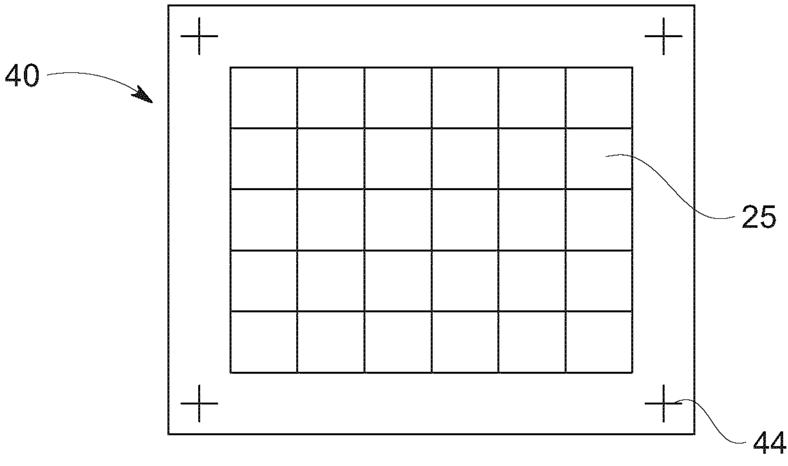
FIG. 13B depicts a transparent poly-CMUT array in the form of a matrix (2D) showing markers or fiducials on the corners of the array for image processing and registration.

Surgical application. Transparent poly-CMUTs arrays (x-ray or optically transparent) can be used for assisted surgery in some embodiments, with ultrasound images generated at the same time as other medical imaging modalities such as x-rays, magnetic resonance imaging (MRI), and/or computer tomography (CT) to create an augmented reality model of a patient anatomy that can be used for doctors during surgery, for instance during spinal surgery. FIGS. 13A and 13B illustrate an array 41 of poly-CMUTs 15. Substrate 14 is selected from x-ray or optically transparent materials such as Kapton, Polyimide, Plexiglass, or Lexan. This allows the surgeon or diagnostic instrument to "see through" the array even while that array reads and provides an additional layer of data regarding the tissue being manipulated or studied.

Figure 11:
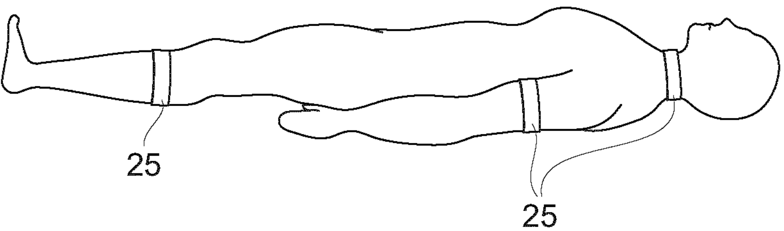
FIG. 11 is an illustration of certain positioning of poly-CMUT fabric is used for real time ultrasonic data gathering from a human body.

In embodiments, transparent poly-CMUTs arrays fabricated on transparent and flexible substrates allow a continuous acquisition of ultrasound images during motion of patients or other materials with curved surfaces. Examples of such wearable array forms 25 are shown in FIG. 11.

Bandage for wounds. In embodiments of the invention, a poly-CMUT array is fabricated into a bandage used to cover wounds during healing. For this purpose, a flexible substrate is used so that it can conform better to tissue. This poly-CMUT array bandage is also capable of monitoring tissue repair and delivering energy to the tissue under repair to increase the speed of the healing process.

In another embodiment, the poly-CMUT array bandage is used to cavitate fluid in the tissue to support debridement.

Ultrasound benefits the healing of wounds through the deposition of ultrasound energy at the site of a wound. Wounds include cuts, abrasions, burns, bruises to soft tissue. Wounds also includes fractures and breaks of bones. Treatment can include debridement to remove necrotic and senescent tissues as well as foreign and infected materials from a wound. Treatment can also include low-frequency and low-intensity ultrasound to actively promote would healing. Frequencies of the ultrasound include kilohertz to megahertz frequencies.

When monitoring a dynamic event, such as fluid through a vessel, it is advantageous to record the acoustic emissions of the event. This includes medical applications, such as blood through a blood vessel, to non-medical applications, such as oil through a pipeline. Some abnormalities of dynamic events, such as rupture of the vessel, cause a characteristic acoustic emission. The wearable poly-CMUT patch can detect these acoustic emissions and relay them to the controller and subsequently the smartphone to notify an operator. It is also possible to fabricate a single device from a number of poly-CMUT elements with different sizes, shapes or material properties in order to achieve a range of acoustic frequencies they are most sensitive to. This will allow a wider range of acoustic emissions to be detected. Another embodiment is to use the coupler for wireless power transfer in FIG. 10C to convert an acoustic emission into a radiowave without the need for electronics to perform the conversion.

Figure 12A:
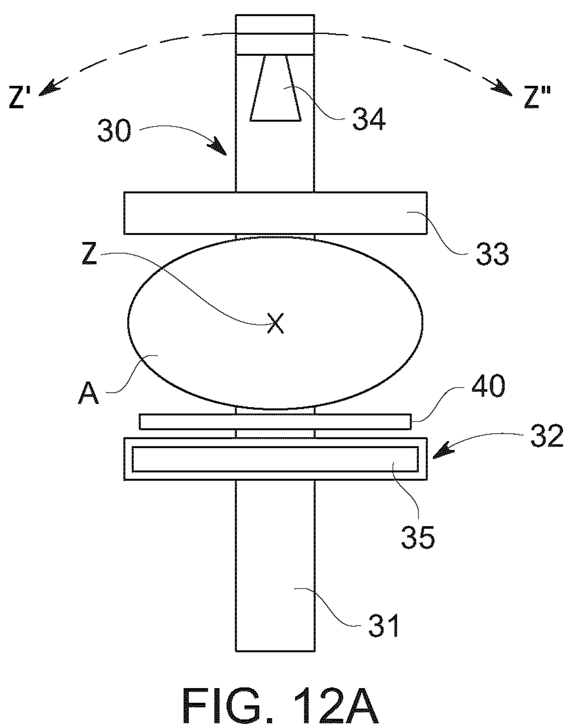
FIG. 12A depicts a basic structure mammography scanner according to a first embodiment of this document, where a transparent poly-CMUT array is integrated into the system.

Diagnostic Instrumentation. In other embodiments, a hybrid integration of transparent poly-CMUTs arrays combines x-rays, ultrasound, photoacoustics, elastography, and/or a combination thereof, in a single system. As shown in FIG. 12A, breast tissue A under examination using Mammography device 30, is subject to both X ray and ultrasonic wavelengths to achieve a more informative diagnosis. In embodiments, the combination of poly-CMUT arrays and other modalities is achieved by retrofitting existing medical equipment as might result in the instrument 30 shown in FIG. 12B. In other embodiments, the combination instrument is created de novo. In embodiments, the poly-CMUT array forms an x-ray transparent component of a mammography machine, adding an additional layer of readout and data to the x-ray signals travelling through breast tissue.

Chemical and Biological Sensing. A wearable poly-CMUT patch can be used to for chemical and biological sensing by functionalizing the membrane of the poly-CMUT element. A functionalized membrane is sensitive to the presence of a chemical or biological substance that changes the mass loading of the membrane. For example, the resonant frequency of the poly-CMUT element depends on the material properties (e.g., mass, stiffness and viscosity) of the membrane, analogous to a drum. In the presence of a particular chemical or biological substance intended to be "sensed", the functionalized membrane can absorb some of the material and its physical properties will be changed thereby. The change in material properties can be detected, for example, by a change in the frequency, bandwidth, or amplitude of the resonant frequency. In particular, it is known that the change in resonant frequency is proportional to the relative change in the mass of the membrane. The poly-CMUT is particularly well suited for this application because it has relatively low inherent mass so it can result in larger frequency changes and therefore achieve high accuracy of measurement of the substance. Moreover, compared to cantilever based sensors with similar active areas, the vacuum sealed cavity of a poly-CMUT is subject to smaller damping which translates into a higher quality factor and higher accuracy in measuring a frequency shift. Moreover, the poly-CMUT can operate either in fundamental mode, with a membrane flexing symmetrically with the center of the membrane with greatest amplitude, or in other modes, such as an asymmetric mode where energy is transferred from the left to the right part of the membrane. Such non-fundamental modes have advantages in the reduced emission of acoustic energy away from the poly-CMUT element.

Heart Monitor. A patch according to embodiments of the invention, sized 5 by 5 cm to 10 by 10 cm in one embodiment, acts as an emitter focusing the ultrasound pulses on skin and a microphone recording the reflected waves, acts as an airborne pulse-Doppler ultrasound system operating in the 20-60 KHz range.

Blood Pressure Monitor. In embodiments of the invention, the poly-CMUT wearable array uses ultrasonic Doppler flow measurements to determine blood pressure non-invasively in a patient population. Blood pressure is measured with the developed poly-CMUT method and compared to an invasive arterial line or to the oscillometric Terumo Elemano™ BP monitor. Blood velocities in the radial artery are recorded by the new poly-CMUT patch during cuff deflation. A sigmoid curve is fitted to a preprocessed velocity signal and the systolic and mean arterial pressures are determined. Applications include pre-eclampsia monitoring in pregnancy and ambulatory blood pressure monitoring in cardiac patients.

Transcranial focused ultrasound (FUS) combined with intravenously circulating microbubbles can transiently and selectively increase blood-brain barrier permeability to enable targeted drug delivery to the central nervous system. This approach may be used in patients with brain tumors, early Alzheimer's disease, and amyotrophic lateral sclerosis. A challenge addressed by at least some embodiments of the present invention is that in order for widespread clinical adoption of FUS-mediated blood-brain barrier permeabilization to occur is the development of systems and methods for real-time treatment monitoring and control, to ensure that safe and effective acoustic exposure levels are maintained throughout the procedures.

For poly-CMUT array fabrication for human contact, after the electrical connections 5 have been formed, the poly-CMUT array is encapsulated by a bio-compatible material such as a poly(p-xylylene) polymer such as parylene, or PVDF, or silicone inside a low-pressure chamber to preserve low pressure in the enclosures (for example, $P=1\times10^{-3}$ Torr). The encapsulating material conformally seals the entire wafer to form a closed cavity, which is vacuum sealed and impermeable.

Now referring to FIG. 7, there is shown an embodiment of a control panel in the form of a printed circuit board with microprocessor 20, beam former 22, memory 23, battery 24, and analog front end electronic component. Hardwiring out to the poly-CMUT panels are depicted at 26. Antenna 27 transmits signal to the user interface (not shown) which will have a graphical component or simple pass/fail readout depending on the application.

The patch thus formed for medical applications is useful for providing information on injuries on site when an accident has occurred. Emergency responders can wrap the injured person in the patch and 'see' the breaks and soft tissue injuries in the victim before initiating transport to medical care. This practice would include checking legs, arms, ribs and spine for breaks, and checking for impact injuries in the skull. As shown in FIG. 11, low blood flow in certain locations may also be identified, indicating compression injuries. Rigidity is maintained by the pillars 16, but the patch is flexible along the longitudinal axis because of the pliancy channels as shown in 3A.

In FIG. 9A, the wearable poly-CMUT patch is connected to the transmit and receiver electronics with a wired communication, and the transmit and receiver electronics are connected to the controller with a wireless communication. The transmit and receive electronics, and thus the connected poly-CMUT transducer, are powered by a battery 24 on the wearable poly-CMUT patch. The controller 50 is then connected to a smartphone 23 with a wireless communication. The user interface software is executed on the smartphone to display ultrasound data or information to the user. In FIG. 9B, the controller incorporates the transmit and receive electronics and is connected to the wearable poly-CMUT patch with wired communication. The transmit and receive electronics, and thus the connected poly-CMUT transducer, are powered by the controller. The controller is connected to the smartphone with a wireless communication. In FIG. 9C, the wearable poly-CMUT patch is connected by wireless communication to the transmit and receive electronics incorporated into the controller.

Transmitter and receiver electronics, sometimes called transceivers, are commercially available from Verasonics, US4US, Interson, and Texas Instruments, for example. For airborne applications and specialized medical applications, 1-dimensional single-line real-time measurements are possible with lower cost hardware, such as Raspberry Pi.

An alternative fabrication of poly-CMUTs involves placing the first polymer-based layer right above the bottom electrode (FIGS. 1C and 1D) to act as an electrical insulating layer. In this process, the sacrificial layer is then deposited and patterned to later become the cavity. Then the top electrode (electrically conductive such as metals or conductive polymers) is deposited and patterned. The last step involves depositing and pattern a second polymer-based layer that covers the top electrode. This fabrication approach decreases the effective distance between electrodes compared to the case where the electrode is placed above the second polymer-based layer.

In this fabrication approach, a conformal deposition of the top electrode is needed (for example, metal sputtering) to maintain electrical uniformity of the top electrode. Alternatively, in some embodiments, the thickness of the top electrode should be at least 1.5 times the thickness of the sacrificial layer if directional deposition methods are used (such as metal evaporation).

Figure 24:
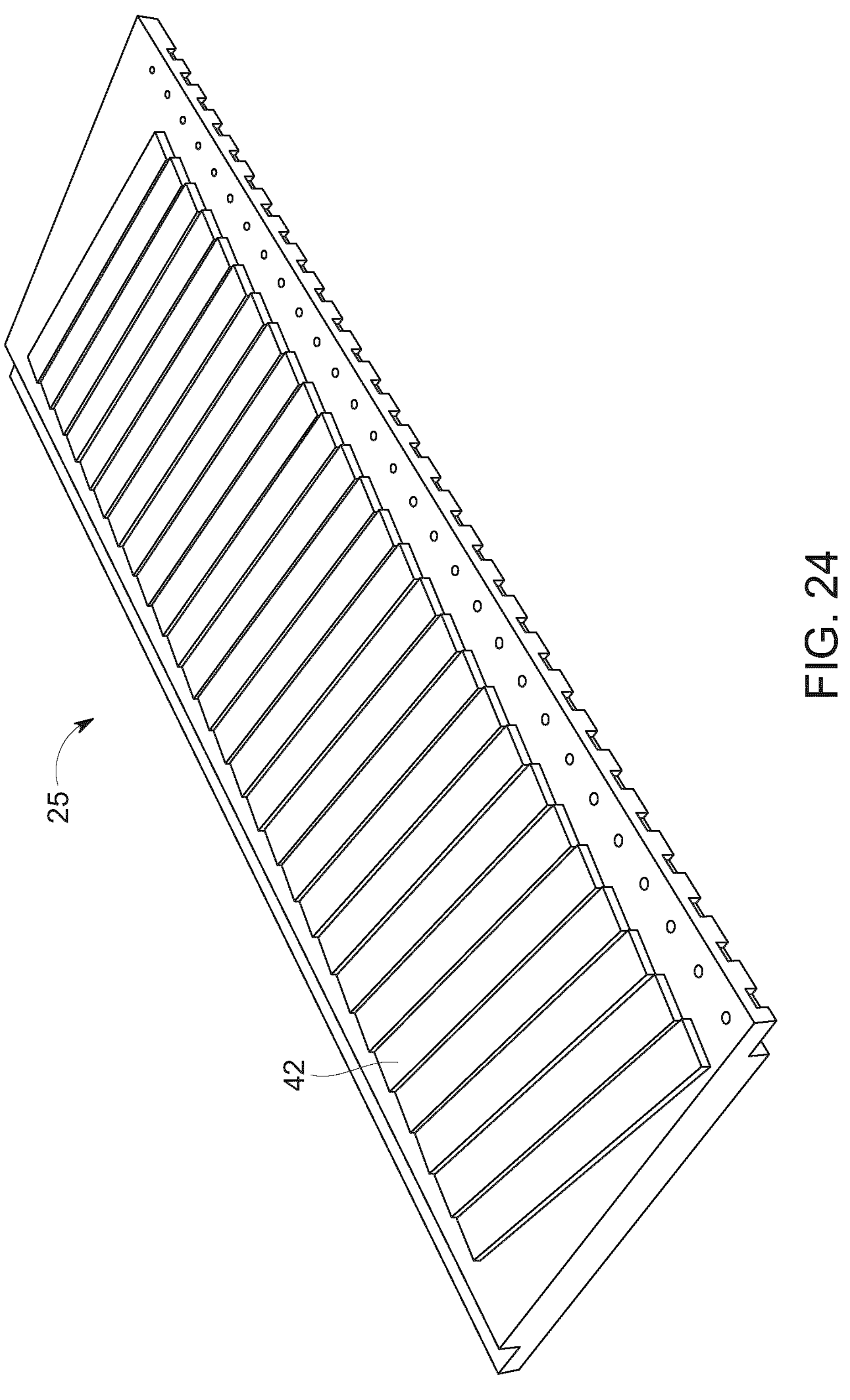
FIG. 24 shows a perspective view of a section of a flexible poly-CMUT array according to one embodiment, with poly-CMUT arrays, physical connectors, and electrical vias.
Figure 25:
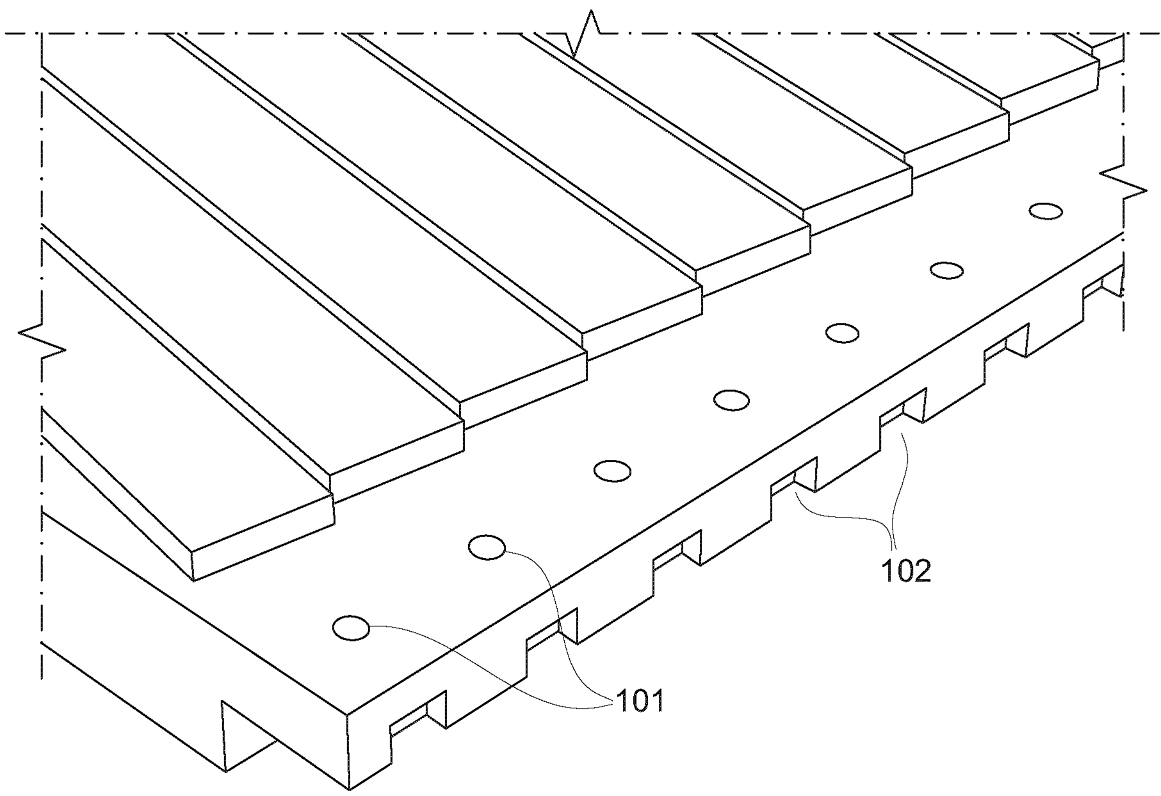
FIG. 25 shows an enlargement view of one side of the poly-CMUT array showing electrical connections points 101, each electrical interconnection point connects electrically to the top electrode of an individual poly-CMUT element 42. There exist mechanical cavities or voids 102 that facilitate the alignment and mechanical fixation to another portion of a flexible poly-CMUT array.

Connecting sections of poly-CMUT arrays. A section of a flexible poly-CMUT array roll 25 with poly-CMUT elements 42 located on the upper side is shown in FIG. 24. Enlarged in FIG. 25 is the cavity side of array 25. Electrical connections points 101 each connect electrically to the top electrode of an individual poly-CMUT array 42. Cavities 102 facilitate the alignment and mechanical fixation to another portion of a flexible poly-CMUT array roll 25 having reciprocal protrusions 104, such as those shown in FIG. 27.

Figure 27:
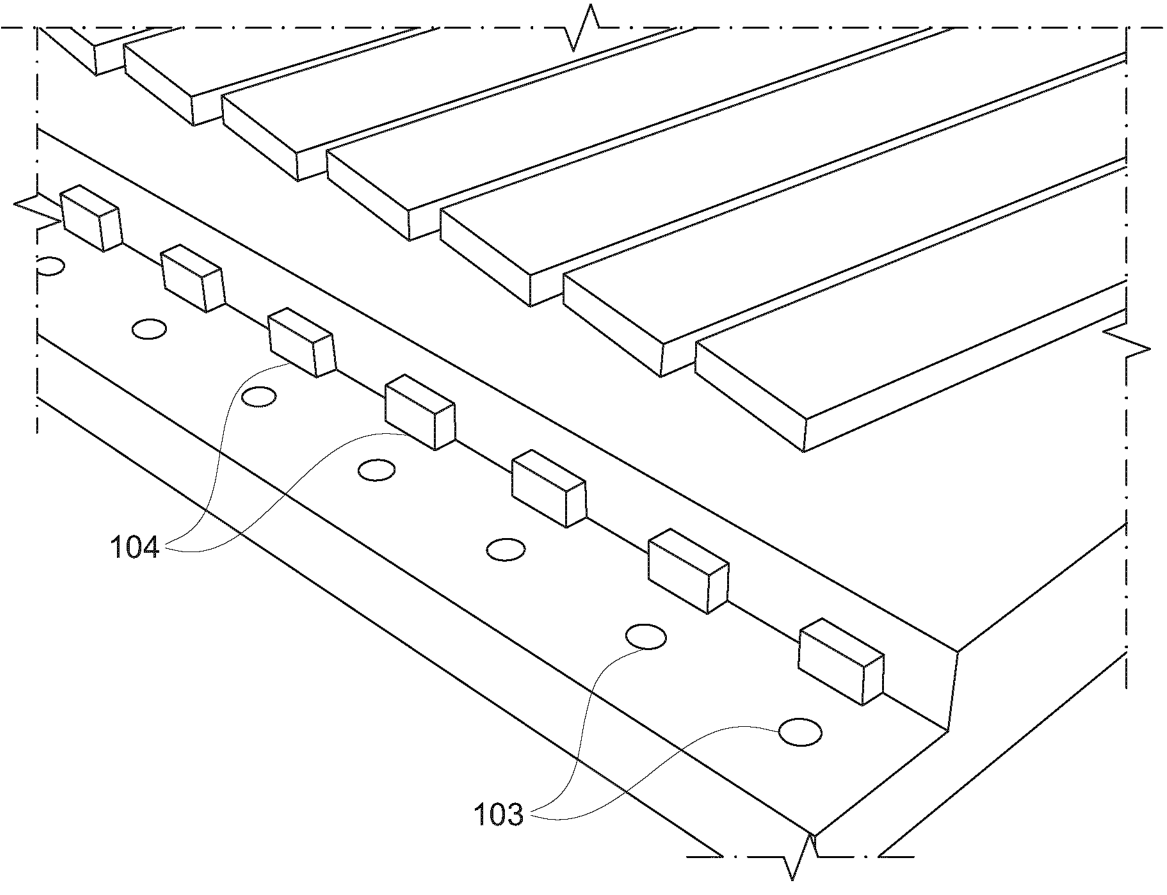
FIG. 27 shows an enlargement view of the same side of the poly-CMUT array 25 as shown in FIG. 26, electrical connections points 103 illustrated near the protrusions 104.

PolyCMUT array roll 25 is also shown in FIG. 26, but with the protrusions side facing toward the viewer. An enlargement of this side is shown in FIG. 27, with electrical connections points 103 illustrated. These connect electrically to the top electrode of an individual poly-CMUT array 42. The mechanical protrusions 102 facilitate the alignment and mechanical fixation to another poly-CMUT array roll 25 in such a way that elements 101 and 103 "snap" in place and the electrical interconnection points 102 and 104 maintain electrical conductivity along the winding axis. The protrusions could have other geometrical shapes, such as a trapezoid shape (not shown) to enhance the mechanical fixation at the edges of the roll.

Figure 28:
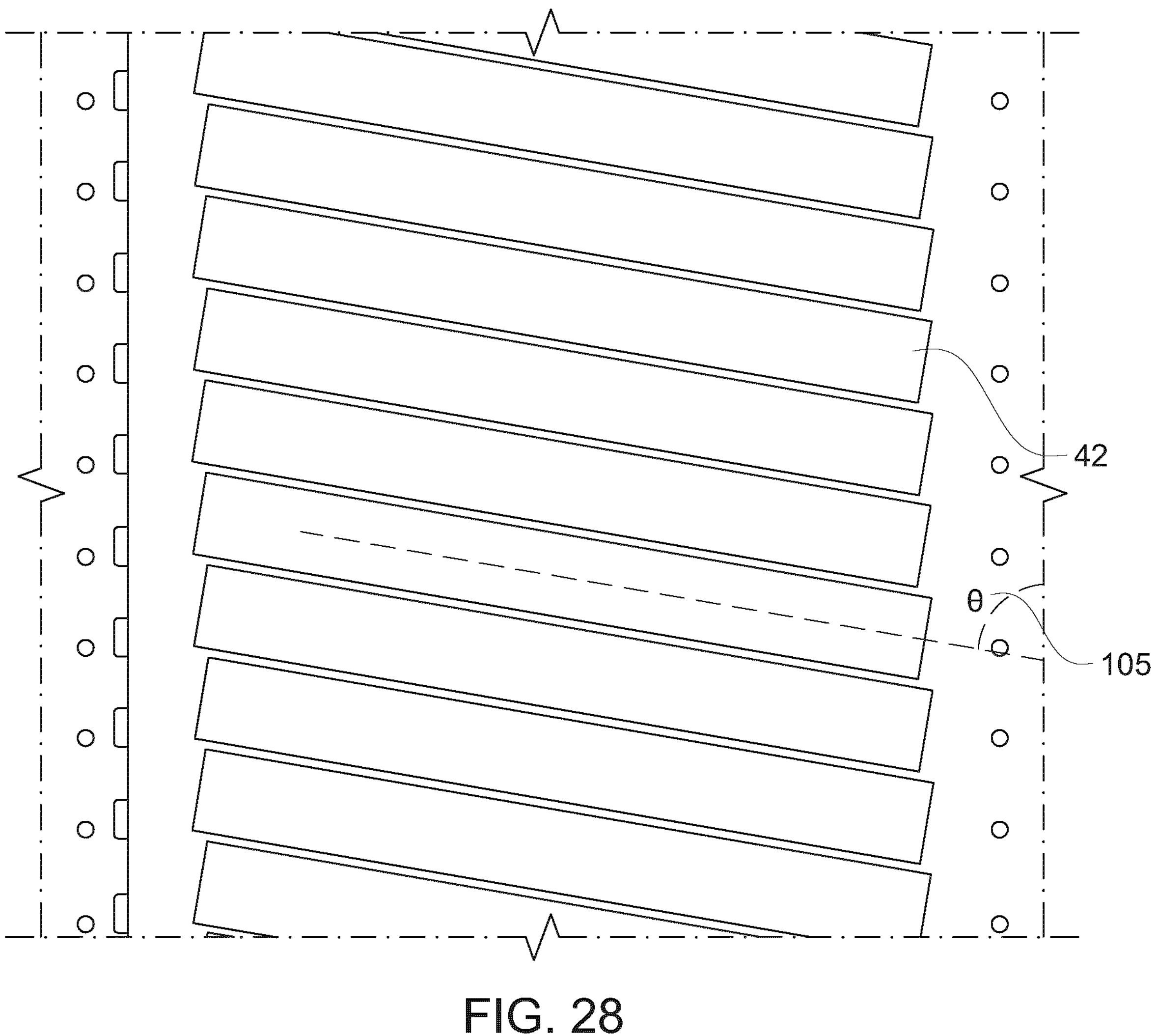
FIG. 28 shows an enlarged view of a poly-CMUT array 25 illustrating the poly-CMUT elements 42 are fabricated at an angle θ 105 with reference with one of the sides.

To accommodate proper connection around cylindrical, curved, or planar surfaces, the poly-CMUT elements 42 are fabricated at an angle θ 105 with reference with one of the sides. This angle θ 105 can range from 1-90 degrees to allow a proper connection of cylindrical, curved or planar surfaces. FIG. 28 shows an enlargement view of a poly-CMUT array roll 25 illustrating this embodiment.

Figure 29:
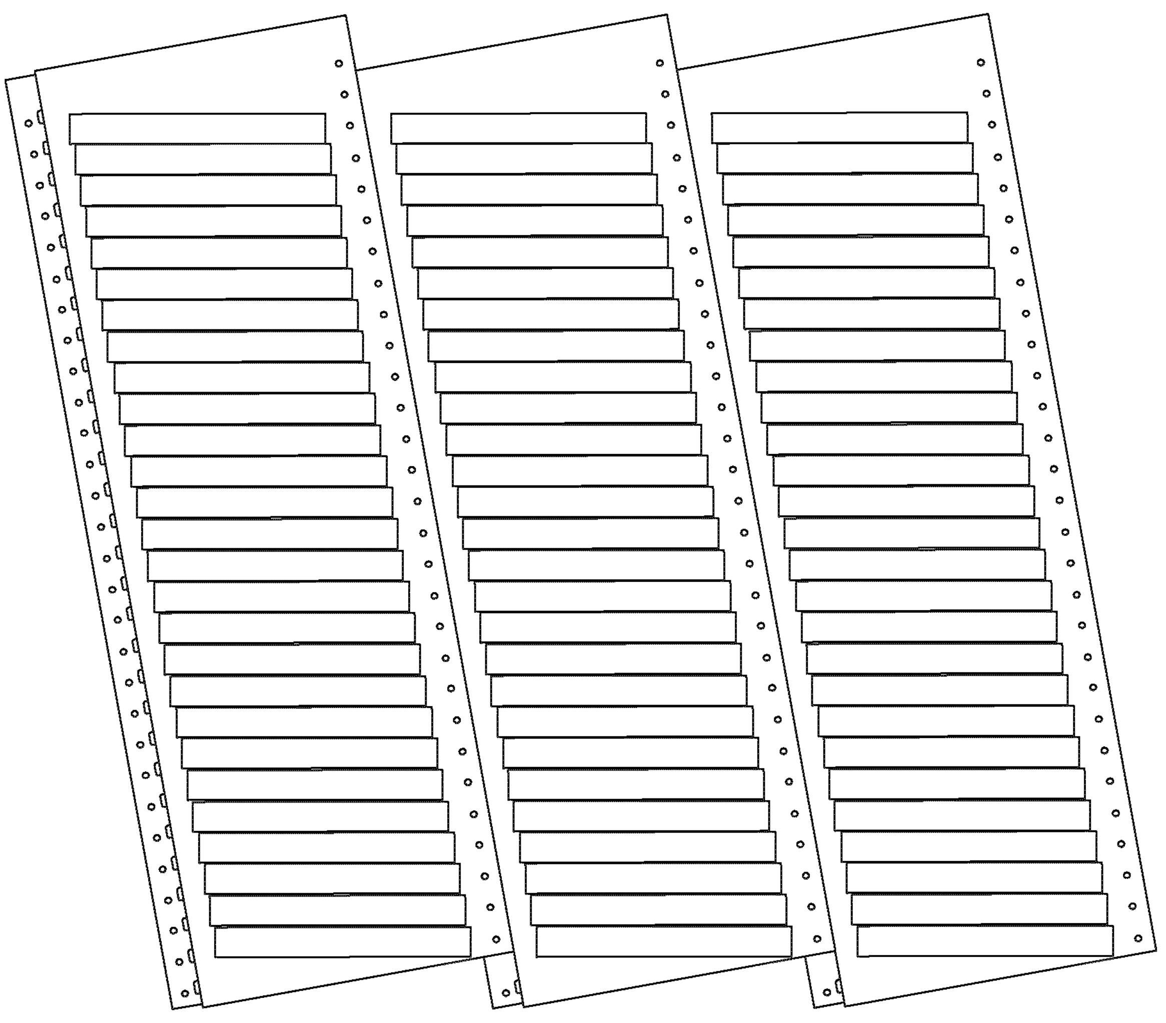
FIG. 29 illustrate three windings or elements of a poly-CMUT array roll are fixed in place and interconnected together.

Several windings of a poly-CMUT array roll fixed in place and interconnected together electrically in such a way that the poly-CMUT elements are aligned is shown in FIG. 29.

Example 1

Finite Element Analysis (FEM) simulations were conducted to assess the feasibility of pillars and "walls" located between poly-CMUT elements to protect the membranes against external pressures. The sample tissue was a modelled human breast. Several assumptions were made to simulate compression forces of a human breast. breast will be assumed to be composed of 3 layers: skin, adipose tissue and glandular tissue. According to [1], the skin is assumed to be 1-3 mm, with glandular and adipose tissues evenly taking up the remaining height. An A-cup with a breast diameter of 11 cm is simplified to a cube with a side length of 7 cm. The clamping force of 100 N is assumed to create an evenly-distributed pressure of 20.4 kPa on the lower plate. All tissue is assumed to be incompressible v~0.5.

A comparison of energy transmission percentages of perpendicular incident x-rays on the thicknesses of different materials is shown in Table 1. Traditional piezoceramic-based ultrasound transducers (e.g., PZT) cannot be used as x-ray transparent sensors. The lead contained in these PZT transducers would attenuate most of the incident x-rays passing through them. Similarly, visible or infrared light cannot simply pass through them.

It was found that materials such as polyimide or polycarbonates are the best candidate as substrates for x-ray transparent poly-CMUT arrays. Polyimide and polycarbonates also exhibit a high degree of optical transparency (comparative table not shown).

For the poly-CMUT electrodes, Aluminum was found to be a good material to achieve x-ray transparency, but not optical transparency. Indium Tin Oxide (ITO) provides a reasonable compromise between x-ray transparency (for electrodes) and optical transparency.

FIG. 12A depicts the front view of the basic structure of a mammography scanning system 30 according to a first embodiment. The mammography scanning system 30 comprises a support device 31, a bottom compression device 32 a top compression device 33, an x-ray emitter 34, an x-ray detector 35 and a transparent poly-CMUT system 40 integrated into the system. In this particular example, a breast A is located in the space between the bottom compression device 32 and the top compression device 33. Either of the compression devices can be slid along the long axis of the support device 31, and the support device 31 can be rotated on the axis Z along the trajectory Z'-Z" to allow the inspection of breast A in a different orientation. The transparent poly-CMUT system 40 can be located either close to the bottom compression device 32 or to the top compression device 33.

Figure 12B:
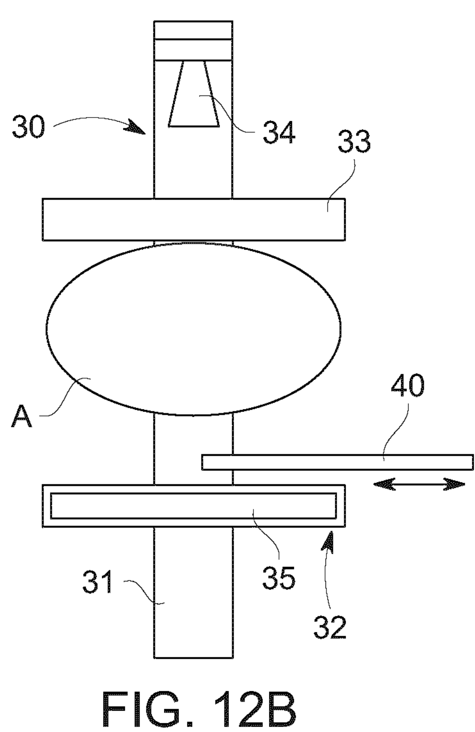
FIG. 12B depicts a basic structure mammography scanner according to a separate embodiment where a transparent poly-CMUT array can be slid or placed in position in existing mammography scanners for retrofitting purposes.
Figure 12C:
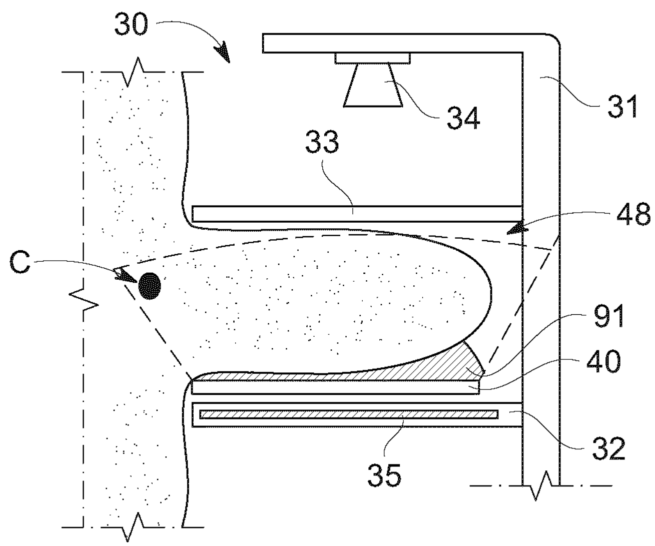
FIG. 12C shows a mammography system with a breast compressed and a transparent poly-CMUT array located above the bottom compression pad, the poly-CMUT array (1.5D or 2D array) can be used image the anatomy close to the chest wall thanks to beam steering and focusing capabilities of the array.

FIG. 12B depicts a similar mammography scanning system to FIG. 12A (a few elements omitted for clarity) according to a separate embodiment. In this particular example, the transparent poly-CMUT array 40 can be placed or slid in position (above the bottom compression device 32 or below the top compression device 33) in existing mammography scanners for retrofitting purposes. This transparent poly-CMUT system 40 can also be removed or installed at the time of a patient examination depending on whether ultrasound is required. Alignment and anchoring supports in the form of a ridge or teeth (not shown) are also integrated in the transparent poly-CMUT system 40 and in either of compression devices 32 or 33 for stability and alignment purposes. In this kind of scanning system (x-rays combined with ultrasound), a good alignment between the x-rays detectors 35 and the ultrasound system 40 is paramount to facilitate image registration and processing. This way an x-ray image and an ultrasound scan can be superimposed or combined in recordings and by user interface to reveal abnormalities in the anatomy of the breast A. As seen in FIG. 12C, there is a simplified mammography scanning system like the one illustrated in FIG. 12A, when a 1.5D or a 2D poly-CMUT array 40 is used. In this particular example, the transparent poly-CMUT array 40 can be used to obtain an increased field of view 48 by means of ultrasound beam focusing and steering. This increased field of view 48 would be useful to detect anatomy abnormalities C (such as cancer cells or tumors or internal lesions) that would otherwise go undetected by ordinary mammography systems. Ultrasound coupling gel 91 may be used to facilitate image acquisition of ultrasound signals.

Figure 12D:
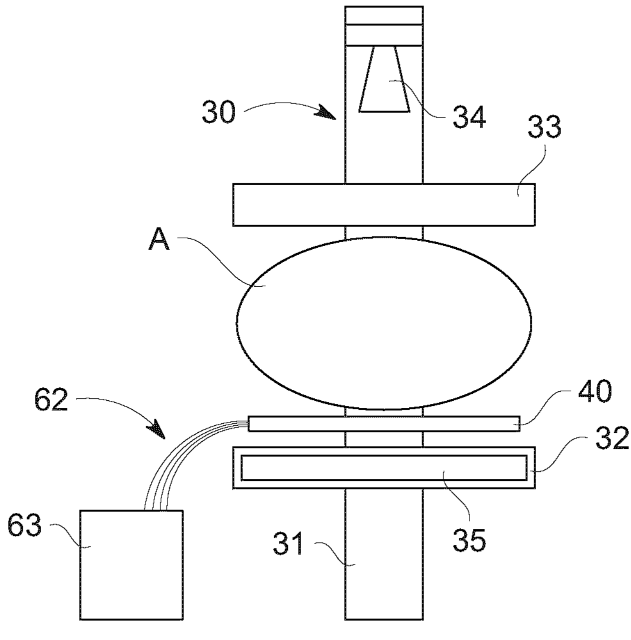
FIG. 12D depicts a basic structure mammography scanner according to a separate embodiment of this document where a transparent poly-CMUT array can be used for photoacoustic imaging purposes.

FIG. 12D depicts a basic structure mammography scanner 30 according to another embodiment of the invention, and similar in structure to that of FIG. 12A. In this scanning system 30, a transparent poly-CMUT array 40 can be used for photoacoustic imaging purposes. The transparent poly-CMUT system has external optical waveguides 62 (e.g., glass fiber) leading to an optical light source 63 where non-ionizing laser pulses typically used for photoacoustic applications are generated and controlled.

FIG. 13A depicts a transparent poly-CMUT scanning system 40. This system comprises a transparent (x-ray or optical transparency) upon which a transparent poly-CMUT array (linear array 1D, parallel linear array 1.5D or a matrix 2D array) is fabricated. Electrical interconnections 26 to the transparent poly-CMUTs elements 15 are located in an edge of the transparent poly-CMUT array 40 leading to a controller 50. Controller 50 includes the microprocessor(s), memory, battery and/or any other power source, any manifolds for wire organization, connectors, relays, and circuits required for receiving, organizing, and transmitting signals to and from the poly-CMUT array 40. The interconnections can be fabricated of x-ray transparent materials such as aluminum or optical transparent materials such as ITO.

FIG. 13B depicts a transparent poly-CMUT array 40 in the form of a matrix (2D). In embodiments, it is a linear array (1D) or an array of linear arrays (1.5D). This array 40 contains fiducial markers 44 located at the corners or at specific areas of the array with the purposes or image overlapping (x-ray and ultrasound) during registration, the fiducials 44 can have equal or different shape and size to facilitate such post-processing. These fiducials 44 can also be used to properly align CMUT elements with the x-rays individual detectors (not shown) to avoid non-uniformities during the acquisition of the x-ray images.

Figure 14A:
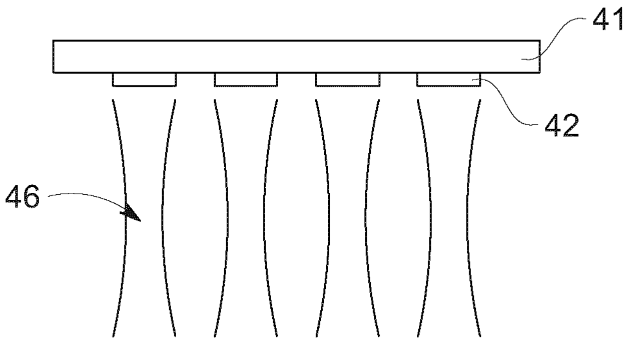
FIG. 14A shows the lateral view of a 1.5D poly-CMUT array, in which each linear array (1D) can be used to image "slices" of the human anatomy.
Figure 14B:
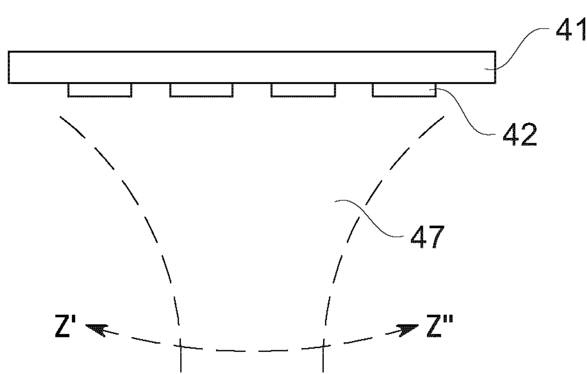
FIG. 14B shows the lateral view of a 1.5D poly-CMUT array, in which each group of linear arrays (1D) can be used to create an ultrasound beam that can be steered and focused to increase the field of view of the final image.

FIG. 14A shows the lateral view of a 1.5D transparent poly-CMUT array 40, showing multiple poly-CMUT linear arrays of poly-CMUTs 15 next to each other. In this configuration, each linear array 42 can be used to create image "slices" 46 of the anatomy of a breast (not shown). In this same configuration and providing the linear arrays are closely spaced, they can be used to focus and steer an ultrasound beam 47 along the trajectory Z'-Z" to increase the field of view of ultrasound images, as illustrated in FIG. 14B.

FIG. 15 shows the cross-sectional view of a transparent ultrasound array 40 showing several poly-CMUT. X-rays passing through different trajectories (paths A-A' to D-D') of the array get attenuated in different percentages due to the different layers (1, 2, 10, 12) of the array 40. To guarantee a uniform x-ray transparency of the array 40, an extra compensation device 60 is helpful in some embodiments. In case the x-ray transparency of the poly-CMUTs array 40 is elevated (e.g., 95% or above), then the compensation device 60 might not be needed.

As shown in FIG. 15, the compensation device 60 is fabricated separately on a different substrate 61 (although with similar properties than that of substrate 14) containing specific heights of an absorbing material 62 that can be used to "correct" the total attenuation of the poly-CMUT array across the different paths (paths A-A" to D-D") and achieve a uniform x-ray attenuation across the entire poly-CMUT array 40. The topography of material 62 is expected to have different heights to "correct" the total x-ray absorption for different paths. Alternatively, different materials or a combination of materials can be used to avoid such a topography and still obtain the same level of x-ray attenuation across the different paths (paths A-A" to D-D"). The compensation device can also be fabricated on the backside of the x-ray transparent poly-CMUT array 40 in other embodiments of the invention.

Figure 16A:
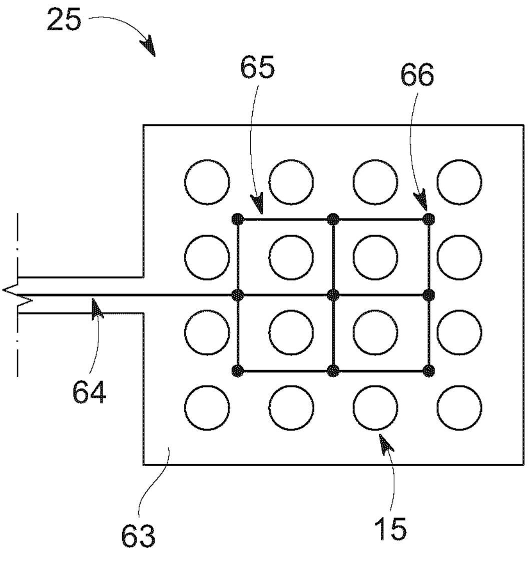
FIG. 16A depicts a photo-acoustic-compatible poly-CMUT array where light waveguides are embedded in the substrate to provide the illumination of the array from the back from a non-ionizing laser source.

FIG. 16A depicts a photoacoustic-compatible poly-CMUT array where light waveguides are embedded in the substrate to provide the illumination of the array from the back coming from a non-ionizing laser source. A main waveguide or a manifold of waveguides 64 is located on one side of the array 25. Internally, waveguides 65 distribute the laser pulses between poly-CMUT elements or cells 15. The outputs 66 of these waveguides are located in spaces between poly-CMUT cells or elements 15 in case that the top electrode (not shown for clarity) of the array is not optically transparent (in the case of Aluminum, for example).

Figure 16B:
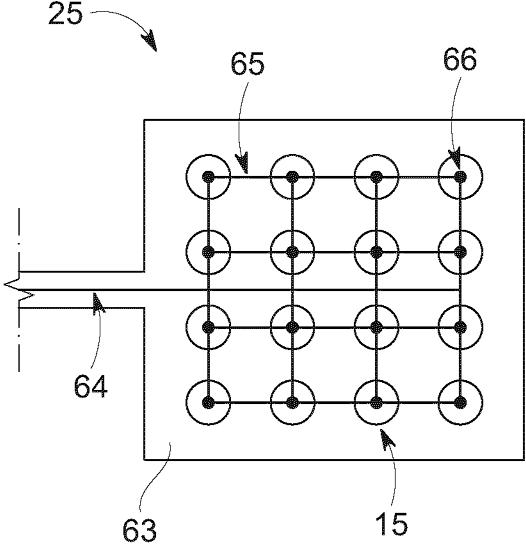
FIG. 16B depicts a photo-acoustic-compatible transparent poly-CMUT array where light waveguides are embedded in the substrate to provide the illumination of the array from the back from a non-ionizing laser.

FIG. 16B depicts a photo-acoustic-compatible poly-CMUT array wherein light waveguides are embedded in the substrate to provide the illumination of the array from the back coming from a non-ionizing laser source. A main waveguide or a manifold of waveguides 64 is located on one side of the array 63. Internally, waveguides 65 distribute the laser pulses between poly-CMUT elements or cells 15. The output 66 of these waveguides are located underneath of poly-CMUT cells or elements 15 in case that the top electrode (not shown for clarity) is optically transparent (if it was made of Indium Tin Oxide, for example).

The described poly-CMUT systems can be used in elastography applications to further enhance the capabilities of the imaging system. Where an ultrasound array can be used to send a wave to mechanically vibrate tissues and record signals coming from shear waves to create a visual image of the stiffness of tissues. The presented transparent poly-CMUT arrays can fulfill these capabilities.

The materials used to fabricate the described polymer-based CMUT arrays are not magnetic, therefore transparent polymer-based CMUT arrays can safely be used with Magnetic Resonant Imaging (MRI) techniques.

Depending on the type of exam required, it might be possible to reduce the intensity of the x-ray radiation while obtaining satisfactory results from the combination of 2 or more medical imaging modalities (e.g., x-rays and ultrasound or x-rays and photoacoustic imaging). This would translate in health advantages for patients and might enable more frequent scans without the extra x-ray dose needed.

At least some embodiments of the present invention will be more readily understood by referring to the following examples which are given to illustrate various embodiments of the invention rather than to limit its scope.

EXAMPLES

Example 1

X-Ray Transparency

To determine the best material suitable for the fabrication of x-ray transparent poly-CMUTs, an initial experiment was performed. Various metals and plastic coated with different conductive materials were tested using a GE Definium™ 8000 x-ray machine including silicon and piezoelectric-based ultrasound probes, printed circuit boards and assorted items from a laboratory environment.

Table 1 is a comparative table showing the energy transmission percentage of incident x-rays depending on the material and its thickness. Table 2 shows the acquisition parameters of the x-ray machine for the images obtained; the settings are typical for imaging soft tissues.

TABLE 1

| | Material | mu/rho @ 20 keV (2E−2 MeV) [cm²/g] | Density [g/cm³] | Transmission [%] Vs. Thickness [um] 0.1 | 1 | 100 | 500 | 1000 | Electrical conductivity [S/m] |
|---|---|---|---|---|---|---|---|---|---|
| Electrode | Lead | 86.36 | 11.34 | 99.03% | 90.67% | | | | 4.55E+06 |
| | Gold | 78.83 | 19.32 | 98.49% | 85.87% | | | | 4.10E+07 |
| | Aluminum | 3.44 | 2.70 | 99.99% | 99.91% | | | | 3.77E+07 |
| | Silver | 18.36 | 10.50 | 99.81% | 98.09% | | | | 6.30E+07 |
| | Copper | 33.79 | 8.96 | 99.70% | 97.02% | | | | 5.96E+07 |
| | Chromium | 20.38 | 7.14 | 99.85% | 98.56% | | | | 7.90E+06 |
| | Titanium | 15.85 | 4.54 | 99.93% | 99.28% | | | | 2.38E+06 |
| | Platinum | 75.74 | 21.45 | 98.39% | 85.00% | | | | 9.43E+06 |
| | Indium | 20.44 | 7.31 | 99.85% | 98.52% | | | | 1.20E+07 |
| | Tin | 0.33 | 7.31 | 100.00% | 99.98% | | | | 9.17E+06 |
| | ITO (In2O3) [3, 4] | 20.00 | 7.14 | 99.86% | 98.58% | | | | 1.30E+04 |
| Substrate | Silicon | 4.46 | 2.32 | | | 90.16% | 59.58% | 35.50% | |
| | Aluminum | 3.44 | 2.70 | | | 91.13% | 62.85% | 39.51% | |
| | SU-8 [1] | 3.00 | 1.20 | | | 96.46% | 83.53% | 69.77% | |
| | Polyimide (kapton) [2] | 0.21 | 1.43 | | | 99.70% | 98.51% | 97.04% | |
| | PMMA | 0.57 | 1.19 | | | 99.32% | 96.66% | 93.43% | |
| | Mylar | 0.58 | 1.40 | | | 99.19% | 96.02% | 92.20% | |
| | Lexan (Polycarbonate) [5] | 0.80 | 1.22 | | | 99.03% | 95.24% | 90.70% | |
| | Borosilicate Glass | 2.30 | 2.23 | | | 95.01% | 77.41% | 59.92% | |

TABLE 2

| ID | 1 | 2 | 3 | 4 | 5 | 6 |
|---|---|---|---|---|---|---|
| CDExp [uGy] | 1.121 | 3.649 | 7.900 | 1.815 | 3.897 | 8.033 |
| UDExp [uGy] | 0.493 | 2.208 | 6.083 | 0.799 | 1.715 | 3.535 |
| Voltage [kV] | 40 | 50 | 60 | 40 | 40 | 40 |
| Exposure time [ms] | 5 | 5 | 5 | 8 | 16 | 31 |
| [mAs] | 1.633 | 1.638 | 1.620 | 2.597 | 5.271 | 10.385 |
| ImageArea DoseProduct | 0.174 | 0.328 | 0.512 | 0.276 | 0.561 | 1.105 |

Figure 23:
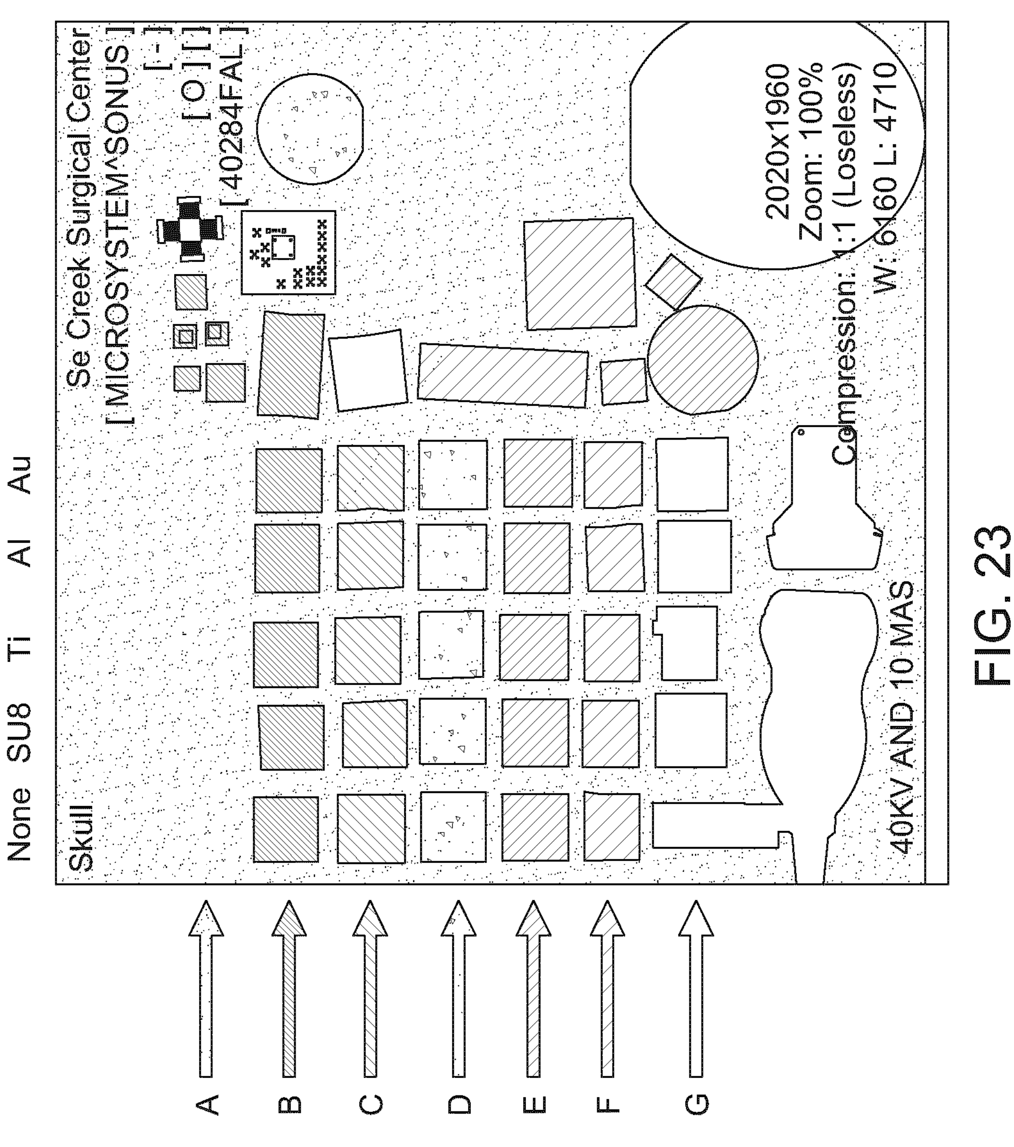
FIG. 23 is a photograph of the calculated x-ray transparency of various materials based on the grayscale level, with background grayscale level of 40, x-ray power 40 KV @ 10 mAs. A is Kapton with was 99.1% X-ray transparency or 42 grayscale level, B was Aluminum at 81.0% x-ray transparency or 81 grayscale level, C was Silicon at 75.5% x-ray transparency or 93 grayscale level, D was Lexan at 88.6% x-ray transparency or 69 grayscale level., E as plexiglass at 89.8% x-ray transparency or 62 grayscale level, F was glass at 65.3% x-ray transparency or 115 grayscale level, and G was stainless steel at 1.39% x-ray transparency or 253 grayscale level. Dark portions are x-ray transparent, white would be x-ray opaque.

As in FIG. 23, the poly-CMUT material Kapton™ polyimide is x-ray transparent (top row indicated by arrow).

FIG. 23 shows the x-ray transparency percentage estimated from the grayscale level of the image. Kapton film shows a transparency of 99.1%. Based on the experimental results, the best material candidate for the fabrication of poly-CMUTs is polyimide (a.k.a. Kapton™) films. This material has excellent physical, thermal and chemical properties that make it possible to fabricate poly-CMUTs on top. The poly-CMUT array can be bent inwards or outwards while maintaining a good mechanical stability, which is ideal for wrapping around non-planar objects. FIG. 23 shows a side-by side comparison of the different materials tested, they include: glass, plexiglass, Lexan™ polycarbonate, silicon, aluminum and Kapton™ polyimide. Polyimide, plexiglass and polycarbonate appear "transparent" in the x-ray image.

Figure 22:
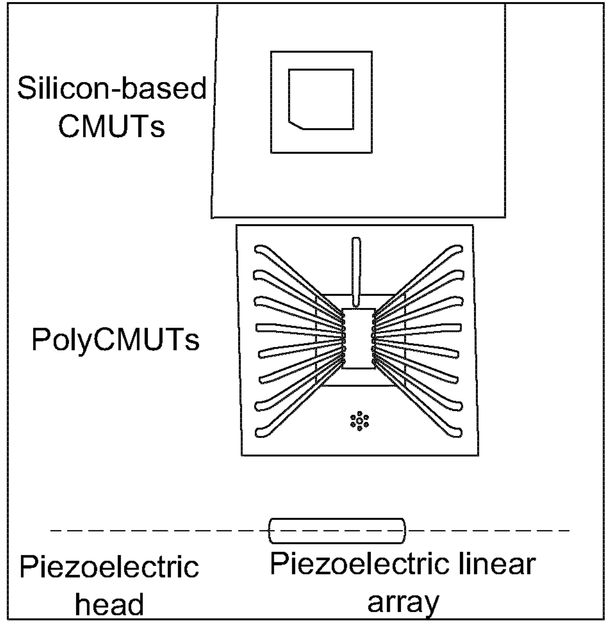
FIG. 22 shows the x-ray transparency of silicon-based poly-CMUT by a line drawing of the x-rayed elements beside a photograph of the x-ray image of the same elements. The upper square in both panels (line drawing and photographic image) is a traditional silicon-based CMUT, the second row is the poly-CMUT according to arrays of at least some embodiments of the invention, and the third row is a traditional piezoelectric-based transducer part. The power was 30 kV @ 160 mAs, which is the average power used for dense breast tissue.
Figure 22:
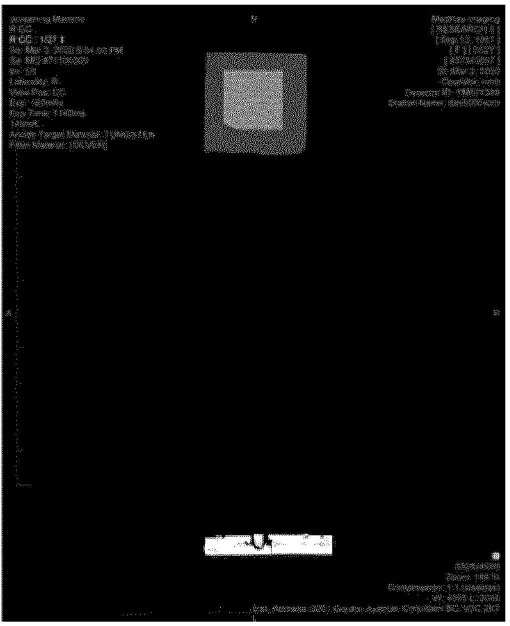

Referring now to FIG. 22. For a subsequent experiment involving x-rays, the mammography device used for testing was the Hologic Selenia Dimensions™ with AWS 8000. A set of three samples were examined: silicon-based ultrasound transducers CMUTs (top), a linear poly-CMUT array (center) and a traditional piezoelectric-based transducers from PZT materials (bottom). For all exposures, the transducers of this example embodiment of the invention (center) did not interfere with the x-rays, whereas traditional silicon-based CMUTs (top) and piezoelectric-based transducers (bottom) did interfere with the x-rays.

Recommended voltage levels were used, doses and filters for this mammography system depending on the average thickness of the compressed human breast of 5 cm. The x-ray image was obtained at 30 kV and 160 mAs (typical settings used for patients with dense breast tissues).

Example 2

Simulations of Pillar Effects

Finite Element Analysis (FEM) simulations were conducted to assess the feasibility of pillars and "walls" between poly-CMUT elements to protect the membranes against external pressures. The results of the testing are shown visually in FIGS. 17-21. The theoretical breast tissue is shown at A. The pillars 16 are indicated.

Figure 17:
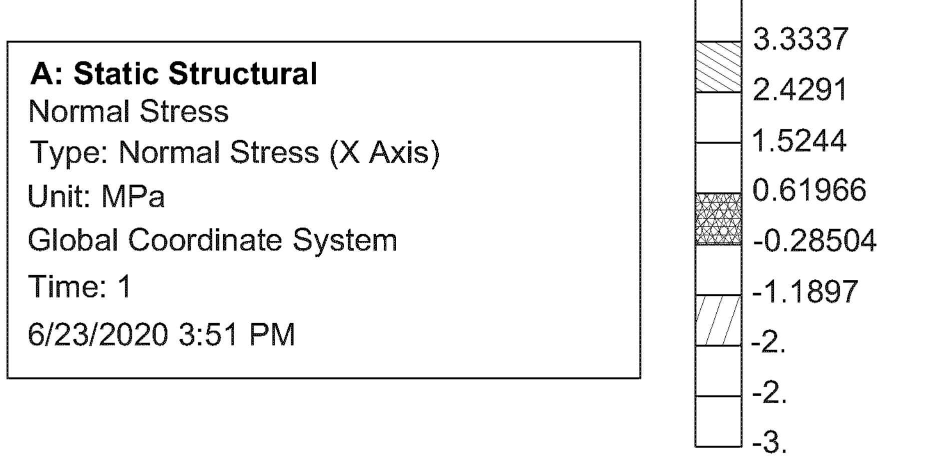
FIG. 17 is a screen shot from an FEM simulation result when a theoretical breast was compressed against a poly-CMUT ultrasound array with pillars measuring 50 μm by 50 μm in height.
Figure 17:
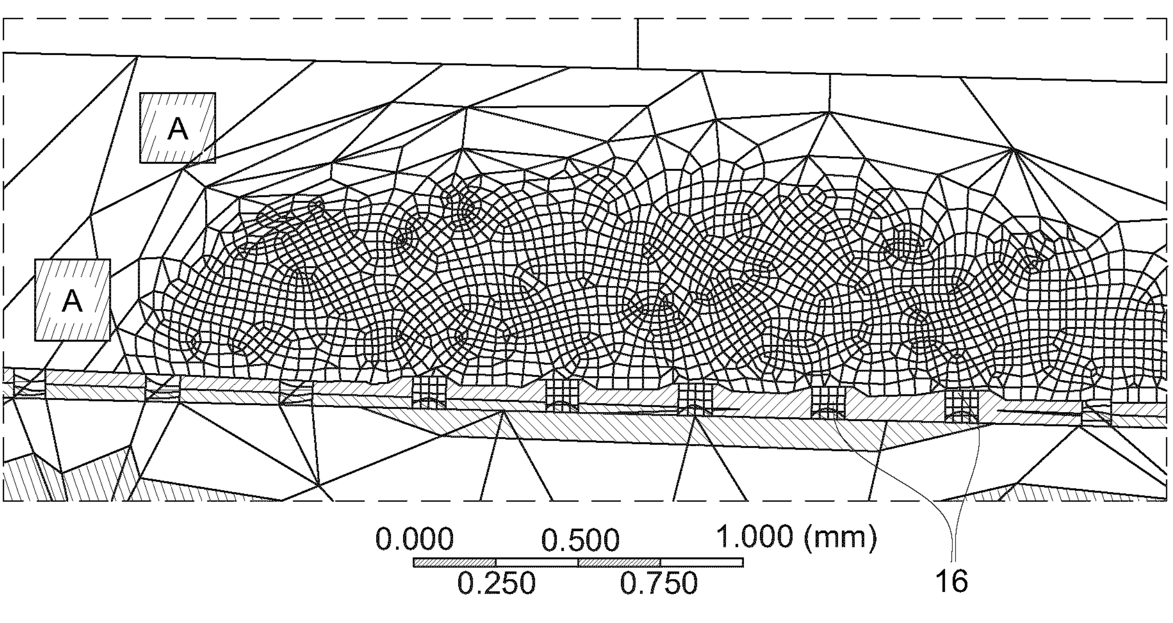

Several assumptions were made to simulate compression forces of a human breast: breast tissue was assumed to be composed of 3 layers: skin, adipose tissue and glandular tissue; skin is assumed to be 1-3 mm, with glandular and adipose tissues evenly taking up the remaining height; an A-cup with a breast diameter of 11 cm is simplified to a cube with a side length of 7 cm; the clamping force of 100 N is assumed to create an evenly-distributed pressure of 20.4 kPa on the lower plate; all tissue is assumed to be incompressible v~0.512. In FIG. 17, FEM simulation when a 100N force is applied on the breast tissue model is shown.

Figure 18:
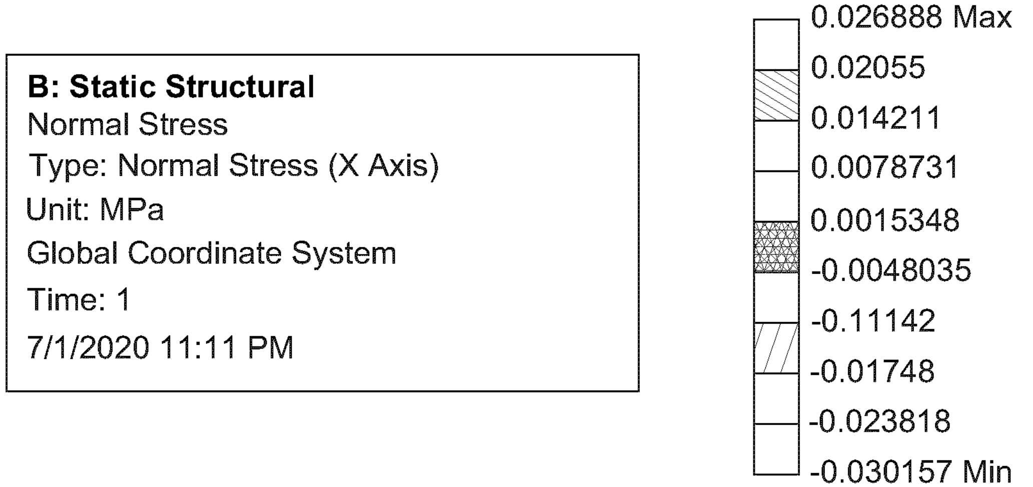
FIG. 18 shows the Finite Element Analysis (FEM) simulation results when a 100 N force is applied on the breast tissue model.
Figure 18:
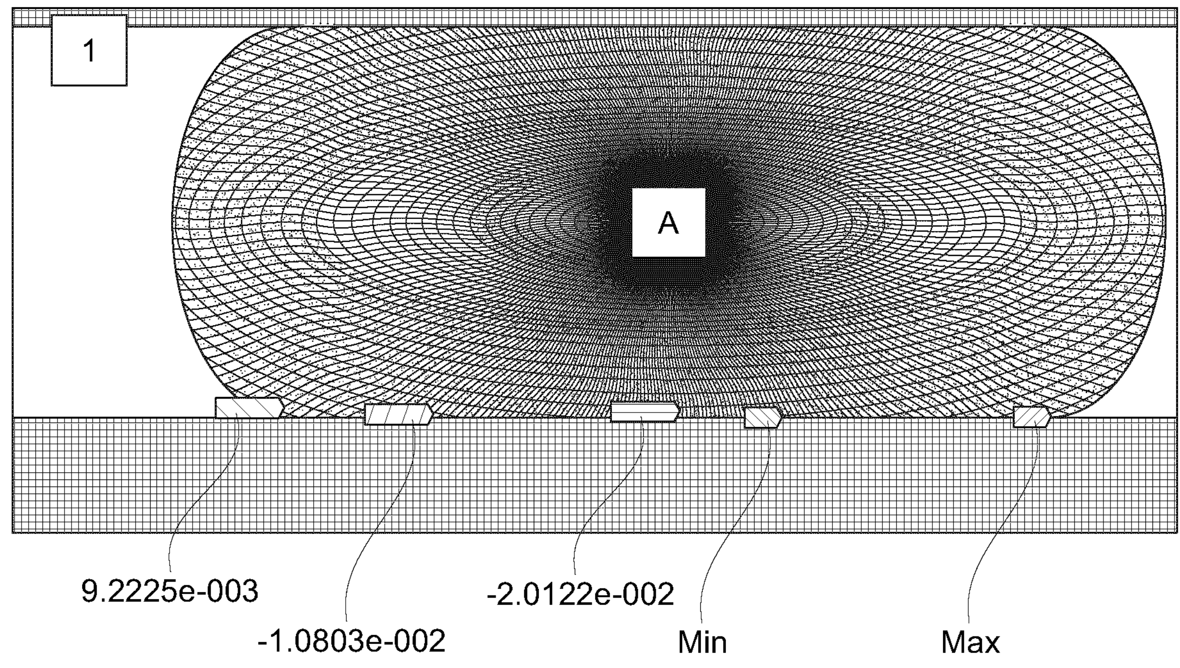

FIG. 18 is a screen shot from an FEM simulation result when a theoretical breast was compressed against a poly-CMUT ultrasound array with pillars measuring 60 μm by 100 μm in height; FIG. 19 is the same but with walls measuring 70 μm by 100 μm in height; FIG. 20 is the same but with walls measuring 50 μm by 250 μm in height; and FIG. 21 with walls measuring 50 μm by 50 μm in height.

Table 3 shows the assessment of the different FEM results obtained. Protective walls will fail to prevent damage to the poly-CMUTs if they measure only 50 μm in width and 50 μm tall. In contrast, protective walls measuring 50 μm in width and 100 μm or above in height will protect the poly-CMUT elements.

TABLE 3

Materials and X-ray Transparency

| Dimensions (microns) | Max Simulated Stress (MPa) | Min Simulated Stress (MPa) | Tensile Strength (MPa) | $\sigma_{crit, theoretical}$ (MPa) | Skin Deflection (pass/fail) |
|---|---|---|---|---|---|
| 50 × 100 | 0.95 | −1.94 | 2 | −103 | pass |
| 60 × 100 | 1.01 | −1.39 | 2 | −148 | pass |
| 70 × 100 | 0.965 | −1.14 | 2 | −72.9 | pass |

TABLE 3-continued

| Materials and X-ray Transparency | | | | | |
|---|---|---|---|---|---|
| Dimensions (microns) | Max Simulated Stress (MPa) | Min Simulated Stress (MPa) | Tensile Strength (MPa) | $\sigma_{crit, theoretical}$ (MPa) | Skin Deflection (pass/fail) |
| 50 × 250 | 2.32 | −2.97 | 2 | −16.4 | pass |
| 50 × 50 | 1.05 | −2.35 | 2 | −411 | fail |

+ tensile,
− compressive

While preferred embodiments have been described above and illustrated in the accompanying drawings, it will be evident to those skilled in the art that modifications may be made without departing from this disclosure. Such modifications are considered as possible variants comprised in the scope of the disclosure.

REFERENCES

[1] Oralkan, O. et al. Capacitive micromachined ultrasonic transducers: Nextgeneration arrays for acoustic imaging? Ultrasonics, Ferroelectrics and Frequency Control, IEEE Transactions on 49, 1596-1610 (2002).

[2] S. Erguri, Y. Huang, X. Zhuang, O. Oralkan, G. G. Yarahoglu, and B. T. Khuri-Yakub, “Capacitive micromachined ultrasonic transducers: fabrication technology,” Ultrasonics, Ferroelectrics and Frequency Control, IEEE Transactions on, vol. 52, no. 12, pp. 2242-2258, 2005.

[3] A. Bozkurt, I. Ladabaum, A. Atalar, and B. T. Khuri-Yakub, “Theory and analysis of electrode size optimization for capacitive microfabricated ultrasonic transducers,” IEEE Transactions on Ultrasonics, Ferroelectrics, and Frequency Control, vol. 46, no. 6, pp. 1364-1374 November 1999.

[4] M. M. Chang, M. T. Deng, J. T. Gwo, J. D. Mai and E. Hsu, “Polymer-based Capacitive Micromachined Ultrasonic Transducers (CMUT) for Micro Surgical Imaging Applications,” 2006 1st IEEE International Conference on Nano/Micro Engineered and Molecular Systems, Zhuhai, pp. 61-65, 2006.

[5] D. A. Hutchins, D. R. Billson, R. J. Bradley, K. S. Ho. Structural health monitoring using polymer-based capacitive micromachined ultrasonic transducers (CMUTs). Ultrasonics, vol. 51, no. 8, pp. 870-877, 2011.

[6] H. Lorenz, M. Despont, N. Fahrni, N. LaBianca, P. Renaud, and P. Vettiger, “SU-8: a low-cost negative resist for MEMS,” J. Micromech. Microeng., vol. 7, no. 3, p. 121, 1997.

[7] C. Liu, “Recent Developments in Polymer MEMS,” Adv. Mater., vol. 19, no. 22, pp. 3783-3790 November 2007

[8] Y. P. Li, C. D. He, J. T. Zhang, J. L. Song, W. D. Zhang, and C. Y. Xue, “Design and Analysis of Capacitive Micromachined Ultrasonic Transducers Based on SU-8,” Key Engineering Materials, vol. 645-646, pp. 577-582, May 2015.

[9] Joseph, J., Singh, S. G. & Vanjari, S. R. K. Fabrication of SU-8 based Capacitive Micromachined Ultrasonic Transducer for low frequency therapeutic applications. in 2015 37th Annual International Conference of the IEEE Engineering in Medicine and Biology Society (EMBC) 1365-1368 (2015).

[10] Chiou, D.-Y., Chen, M.-Y., Chang, M.-W. & Deng, H.-C. Finite element modeling, characterization, and optimization design for the polymer-typed capacitive micro-arrayed ultrasonic transducer. Microsyst Technol 14, 787 is a 797 (2008).

[11] C. F. Dalziel, “Electric shock hazard,” IEEE Spectrum, vol. 9, no. 2, pp. 41-50, February 1972.

[12] A. Gefen and B. Dilmoney, “Mechanics of the normal woman’s breast,” THC, vol. 15, no. 4, pp. 259-271, July 2007.

The invention claimed is:

1. An apparatus comprising:

(i) a substrate; and (ii) an array of polymer-based capacitive micromachined ultrasonic transducers positioned on the substrate, the array comprising a first row of the transducers and electrical interconnections electrically connecting the transducers of the first row in series; and (iii) two rows of walls extending from a same side of the substrate as the transducers of the first row and positioned such that the first row of the transducers is between the two rows of walls, wherein the walls are taller than the first row of transducers.

2. The apparatus of claim 1, wherein the array further comprises additional rows of the transducers and electrical interconnections electrically connecting the transducers of any one of the additional rows in series with each other, and wherein the rows are positioned in parallel with each other.

3. The apparatus of claim 2, further comprising electrical interconnections spanning across the rows such that the transducers comprise an electrically interconnected matrix, wherein the transducers comprise dyed polymer, wherein a portion of the side of the substrate on which the array of transducers is positioned is adhesive, and wherein the portion that is adhesive is located around the array.

4. The apparatus of claim 1, wherein the substrate is selected from the group consisting of an elastic fabric, a metal foil and a non-magnetic substrate.

5. The apparatus of claim 1, wherein the substrate is flexible.

6. The apparatus of claim 1, wherein the substrate is substantially transparent to at least one of ultraviolet light, visible light, and infrared light.

7. The apparatus of claim 1, wherein the substrate is selected from the group consisting of polyimide, polycarbonate, polymethyl methacrylate, aluminum and Indium Tin Oxide.

8. The apparatus of claim 1, wherein the array further comprises additional rows of the transducers and electrical interconnections electrically connecting the transducers of any one of the additional rows in series with each other, wherein the apparatus further comprises additional rows of walls extending from a same side of the substrate as the additional rows of the transducers and positioned such that the additional rows of the transducers are respectively between the additional rows of walls, wherein the additional rows of walls are taller than the additional rows of the transducers, and wherein the apparatus further comprises columns of walls extending from the same side of the substrate as the transducers and that cross the rows of walls, wherein columns of the transducers are respectively between the columns of walls, wherein the columns of walls are taller than the transducers.

9. The apparatus of claim 1, wherein the walls reduce acoustic cross-coupling, and wherein the walls have a height of at least 50 μm.

10. The apparatus of claim 1, wherein at least some of the walls are segmented, and wherein at least some of the walls extend linearly or in a zig-zag pattern across the substrate.

11. The apparatus of claim 1, wherein at least some of the walls are mechanically reinforced, wherein the walls that are mechanically reinforced comprise reinforced portions and non-reinforced portions in which the reinforced portions are thicker than the non-reinforced portions, and wherein at least the ends of the walls comprise the reinforced portions, wherein the walls that are mechanically reinforced comprise reinforced portions and non-reinforced portions in which the reinforced and non-reinforced portions have different cross-sections, and wherein the walls that are mechanically reinforced comprise reinforced portions and non-reinforced portions in which the reinforced and non-reinforced portions are manufactured from different materials.

12. The apparatus of claim 1, further comprising acoustic micro lenses, the acoustic micro lenses comprising one or more layers of material deposited between a top of the walls and a top of the transducers.

13. The apparatus of claim 1, wherein the substrate comprises a tape for applying in rows to an object, wherein the tape comprises top bondpads along a top surface of the tape, bottom bondpads along a bottom surface of the tape, and vias through the tape respectively electrically connecting pairs of the top and bottom bondpads, wherein the bondpads are positioned such that the adjacent rows of the tape overlap each other and the top bondpads of one of the adjacent rows contact the bottom bondpads of the other of the adjacent rows, wherein the top and bottom bondpads respectively extend along edges of the top and bottom surfaces, wherein the rows of the transducers extend non-orthogonally relative to edges of the tape to facilitate the applying of the tape to a curved surface, wherein the tape comprises a relief alignment lock-in pattern positioned to facilitate overlapping of the bondpads, and wherein the relief alignment lock-in pattern comprises a protrusion on one of the top and bottom surfaces and a corresponding recess in the other of the top and bottom surfaces.

14. The apparatus of claim 1, further comprising light waveguides embedded in the substrate.

15. The apparatus of claim 14, wherein the light waveguides terminate in the transducers.

16. The apparatus of claim 14, wherein the light waveguides terminate in the substrate outside of the transducers.

17. The apparatus of claim 1, further comprising:

(i) a wireless transmitter communicatively coupled to the transducers; and (ii) a battery electrically coupled to the wireless transmitter and to the transducers, wherein the wireless transmitter is configured to wirelessly transmit ultrasound data obtained using the transducers to a controller.

18. The apparatus of claim 1, wherein the apparatus is used for at least one of structural integrity testing, pipeline monitoring, and hydraulic testing.

19. The apparatus of claim 1, wherein the apparatus is used for aircraft wing non-destructive testing.

20. The apparatus of claim 1, wherein the apparatus is used for a medical diagnostic.

21. The apparatus of claim 1, wherein the apparatus is used for performing an ultrasound of a breast while a mammography is being performed on the breast.

22. The apparatus of claim 1, wherein the apparatus is used for at least one of:

(i) chemical and/or biological testing;

(ii) heart monitoring;

(iii) blood pressure monitoring; and (iv) cleaning debris, wherein the debris comprises one or more of dirt, dust, water, ice or blood.

23. The apparatus of claim 1, wherein the apparatus is used for generating an ultrasonic signal while an x-ray image is obtained through the apparatus.

24. The apparatus of claim 1, wherein the substrate is at least 77.4% transparent to ionizing radiation.

25. The apparatus of claim 24, wherein the ionizing radiation is x-rays.

26. The apparatus of claim 25, further comprising fiducial markers located on at least one corner of the substrate, wherein the fiducial markers are less transparent to x-rays than the substrate.

* * * * *